(12) United States Patent
Cariola et al.

(10) Patent No.: US 10,137,269 B2
(45) Date of Patent: Nov. 27, 2018

(54) CUSHION-TO-FRAME COMPONENT FOR AN INTERFACING STRUCTURE

(75) Inventors: Melanie Lucia Cariola, Epping (AU); Andrew Hung, Peakhurst (AU); Alicia Kristianne Wells, Narrabeen (AU); Thomas Kirby, Darling Point (AU); Memduh Guney, Killara (AU); Craig David Edwards, Annandale (AU); Lee James Veliss, Freshwater (AU)

(73) Assignee: RESMED LIMITED, Bella Vista (AU)

( * ) Notice: Subject to any disclaimer, the term of this patent is extended or adjusted under 35 U.S.C. 154(b) by 747 days.

(21) Appl. No.: 13/396,270

(22) Filed: Feb. 14, 2012

(65) Prior Publication Data
US 2012/0204879 A1    Aug. 16, 2012

Related U.S. Application Data

(60) Provisional application No. 61/457,751, filed on May 26, 2011, provisional application No. 61/457,261, filed on Feb. 14, 2011.

(51) Int. Cl.
*A61M 16/06*    (2006.01)

(52) U.S. Cl.
CPC ........ *A61M 16/06* (2013.01); *A61M 16/0611* (2014.02); *A61M 16/0616* (2014.02); *A61M 16/0655* (2014.02); *Y10T 29/49826* (2015.01)

(58) Field of Classification Search
CPC .............. A61M 16/06; A61M 16/0611; A61M 16/0633; A61M 16/0622; A61M 16/0655; Y10T 29/4998; B29C 44/06; B29C 44/1242; B29C 44/1219; B29C 44/1204; A62B 18/02

USPC ........... 128/206.21, 206.24, 206.28, 207.13, 128/207.14, 207.18; 24/457, 470; 264/245.1, 46.4
See application file for complete search history.

(56) References Cited

U.S. PATENT DOCUMENTS

| | | | | |
|---|---|---|---|---|
| 4,707,863 A | * | 11/1987 | McNeal | A61F 9/028 2/436 |
| 7,234,466 B2 | * | 6/2007 | Kwok et al. | 128/207.11 |
| 7,318,439 B2 | * | 1/2008 | Raje et al. | 128/206.24 |

(Continued)

FOREIGN PATENT DOCUMENTS

WO    WO 2006/074517    7/2006
WO PCT/AU2009/000262    3/2009

(Continued)

*Primary Examiner* — Colin W Stuart
*Assistant Examiner* — Douglas Sul
(74) *Attorney, Agent, or Firm* — Nixon & Vanderhye, P.C.

(57) ABSTRACT

An interfacing structure for a mask system includes a cushion component adapted to contact the patient's face in use and a cushion-to-frame component provided to the cushion component. The cushion-to-frame component is structured to secure the cushion component to a mask frame of the mask system. The cushion-to-frame component includes a cushion side adapted to interface with the cushion component and a frame side adapted to interface with the mask frame. The cushion side includes a platform to engage and support the cushion component. The platform provides an engagement surface to engage the cushion component and inner and outer flanges provided to opposing ends of the platform to guide, support and/or retain the cushion component on the platform.

53 Claims, 18 Drawing Sheets

(56) References Cited

U.S. PATENT DOCUMENTS

| | | | |
|---|---|---|---|
| 7,856,980 B2* | 12/2010 | Lang et al. | 128/206.27 |
| 8,550,080 B2* | 10/2013 | McGinnis et al. | 128/206.24 |
| 8,701,667 B1* | 4/2014 | Ho et al. | 128/206.24 |
| 2004/0118406 A1* | 6/2004 | Lithgow et al. | 128/206.24 |
| 2005/0172969 A1* | 8/2005 | Ging | A61M 16/06 128/206.24 |
| 2006/0042629 A1* | 3/2006 | Geist | A61M 16/06 128/206.24 |
| 2006/0169286 A1* | 8/2006 | Eifler et al. | 128/206.21 |
| 2008/0053450 A1* | 3/2008 | Van Kerkwyk et al. | 128/206.24 |
| 2008/0230067 A1* | 9/2008 | Kwok | A61M 16/0666 128/206.24 |
| 2008/0289633 A1* | 11/2008 | Kwok | A61M 16/06 128/206.24 |
| 2009/0107506 A1* | 4/2009 | Collazo et al. | 128/206.21 |
| 2009/0199372 A1* | 8/2009 | Anderson | 24/458 |
| 2010/0006100 A1* | 1/2010 | Eifler et al. | 128/206.24 |
| 2010/0006101 A1* | 1/2010 | McAuley et al. | 128/206.24 |
| 2011/0154623 A1* | 6/2011 | Schmidt et al. | 24/457 |

FOREIGN PATENT DOCUMENTS

| | | |
|---|---|---|
| WO | PCT/AU2009/001144 | 9/2009 |
| WO | WO 2009109004 A1 * | 9/2009 |
| WO | WO 2010015393 A1 * | 2/2010 |

\* cited by examiner

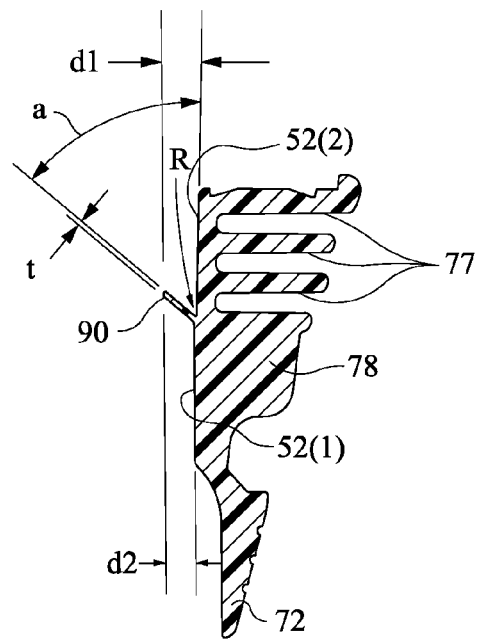
Fig. 10
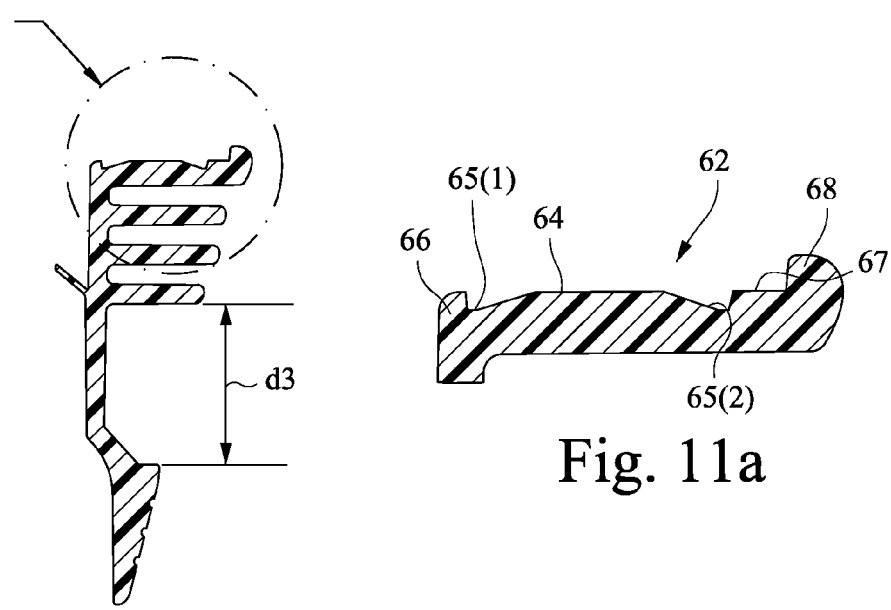
Fig. 11
Fig. 11a

CUSHION-TO-FRAME COMPONENT FOR AN INTERFACING STRUCTURE

CROSS-REFERENCE TO APPLICATION

This application claims the benefit of U.S. Provisional Application Nos. 61/457,261, filed Feb. 14, 2011, and 61/457,751, filed May 26, 2011, each of which is incorporated herein by reference in its entirety.

FIELD OF TECHNOLOGY

The present technology relates to an interface between a human and a piece of equipment, for example respiratory devices that include an interfacing structure.

BACKGROUND OF TECHNOLOGY

In a number of fields, such as respiratory therapy, apparatus for delivery of therapy includes a more rigid component and a soft, cushioning component positioned between the patient and the rigid component.

In the case of a respiratory device, the more rigid component may be a mask frame at least partly defining a nose-receiving chamber. The mask frame may include a flange around its periphery. The cushioning component or interfacing structure may be glued or otherwise coupled to the flange.

The present technology provides alternative arrangements for coupling a cushioning component or interfacing structure to a mask frame.

SUMMARY OF TECHNOLOGY

One aspect of the disclosed technology relates to a cushion-to-frame component structured to facilitate assembly/disassembly of the interfacing structure to the mask frame.

Another aspect of the disclosed technology relates to a cushion-to-frame component structured to enhance retention to the frame.

Another aspect of the disclosed technology relates to a cushion-to-frame component structured to enhance cushion-to-frame seal.

Another aspect of the disclosed technology relates to a cushion-to-frame component structured to enhance durability and/or facilitate manufacture.

Another aspect of the disclosed technology relates to an interfacing structure for a mask system including a cushion component adapted to contact the patient's face in use and a cushion-to-frame component provided to the cushion component. The cushion-to-frame component is structured to secure the cushion component to a mask frame of the mask system. The cushion-to-frame component includes a cushion side adapted to interface with the cushion component and a frame side adapted to interface with the mask frame. The cushion side may include a platform to engage and support the cushion component. The cushion side may include a glue channel to permit the passage of glue and capture excess glue. The platform provides an engagement surface to engage the cushion component and inner and outer flanges provided to opposing ends of the platform to guide, support and/or retain the cushion component on the platform.

Another aspect of the disclosed technology relates to an interfacing structure for a mask system including a cushion component adapted to contact the patient's face in use and a cushion-to-frame component provided to the cushion component. The cushion-to-frame component is structured to secure the cushion component to a mask frame of the mask system. The cushion-to-frame component may be molded in TPE.

Another aspect of the disclosed technology relates to an interfacing structure for a mask system including a cushion component adapted to contact the patient's face in use and a cushion-to-frame component provided to the cushion component. The cushion-to-frame component is structured to secure the cushion component to a mask frame of the mask system. The cushion-to-frame component includes a sealing lip adapted to engage the mask frame and provide a seal. The sealing lip is disposed at an angle and has a length to enhance seal and control ease of insertion or assembly. The sealing lip may also have inner and/or outer radii where it joins the body of the cushion-to-frame component to enhance seal and control ease of insertion or assembly. The sealing lip may also have a surface finish such as frosting or other surface roughening to increase the ease of insertion or assembly.

Another aspect of the disclosed technology relates to an interfacing structure for a mask system including a cushion component adapted to contact the patient's face in use and a cushion-to-frame component provided to the cushion component. The cushion-to-frame component is structured to secure the cushion component to a mask frame of the mask system. The cushion-to-frame component includes a sealing lip adapted to progressively engage the mask frame by adjusting the position of the sealing lip's height on a side wall of the cushion-to-frame component, varying the length of the sealing lip around the perimeter of the cushion-to-frame component, and/or varying the angle of the sealing lip with respect to the inner wall.

Another aspect of the disclosed technology relates to an interfacing structure for a mask system including a cushion component adapted to contact the patient's face in use and a cushion-to-frame component provided to the cushion component. The cushion-to-frame component is structured to secure the cushion component to a mask frame of the mask system. The cushion-to-frame component includes at least one clip portion adapted to engage a respective slot provided on the mask frame. The at least one clip portion extends from a wall of the cushion-to-frame component. The wall includes a rib adjacent each of the side clip portions structured and arranged to engage the mask frame and enhance the force at which a sealing lip adjacent the clip portion engages the frame. The wall may also include additional adjacent ribs to stiffen and control the flexibility of the clip portion.

Another aspect of the disclosed technology relates to a cushion-to-frame component structured to secure a cushion component to a mask frame of the mask system. The cushion-to-frame component may include one or more ribs provided between inner and outer walls of the cushion-to-frame component to enhance rigidity and assist to align the cushion-to-frame component to the frame.

Another aspect of the disclosed technology relates to a cushion-to-frame component that is constructed and arranged to impart a 3-dimensional shape to a 2-dimensional cushion component that is assembled thereto. Furthermore, another aspect of the disclosed technology relates to a process in which a flat cushion component is assembled to a curved cushion-to-frame component, and in which a curved shape is imparted to the flat cushion component.

Another aspect of the disclosed technology relates to an interfacing structure for a mask system including a cushion component adapted to contact a region of the patient's face in use, the cushion component being manufactured to have a two-dimensional shape, and a cushion-to-frame component including a cushion surface constructed and arranged to have a three dimensional shape and to impart that shape to the cushion component when the cushion component is assembled to the cushion surface of the cushion-to-frame component.

Another aspect of the disclosed technology relates to a method for manufacturing an interfacing structure for a mask system. The method includes providing a cushion-to-frame component including a cushion surface having a three-dimensional shape, and assembling a cushion component having a two-dimension shape to the cushion surface of the cushion-to-frame component such that that the cushion-to-frame component imparts its three-dimensional shape to the cushion component.

Other aspects, features, and advantages of this technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various examples of this technology. In such drawings:

FIG. 10 is a cross-sectional view through line 10-10 of FIG. 5;

FIG. 11 is a cross-sectional view through line 11-11 of FIG. 5;

FIG. 11a is an enlarged view of a portion of FIG. 11;

FIGS. 18-1 to 18-3 are schematic views of cushion-to-frame components according to alternative examples of the disclosed technology;

FIGS. 25-1 to 25-5 are perspective views of pad support portions according to alternative examples of the disclosed technology;

DETAILED DESCRIPTION OF ILLUSTRATED EXAMPLES

The following description is provided in relation to several examples (most of which are illustrated, some of which may not) which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

Each illustrated example includes features that may be adapted for use and/or incorporated into the examples and/or components of the interfacing structures described in PCT Application Nos. PCT/AU2009/000262 and PCT/AU2009/

001144, as would be apparent to those of ordinary skill in the art. PCT Application Nos. PCT/AU2009/000262 and PCT/AU2009/001144 are each incorporated herein by reference in its entirety. For example, the foam based interface of the present technology may be retrofit or otherwise provided to cushion frames described in these applications, e.g., the QUATTRO™ mask by ResMed.

While each illustrated example is described as being implemented into a foam-based interfacing structure of the type described in PCT Application Nos. PCT/AU2009/000262 and PCT/AU2009/001144, each illustrated example may be implemented into other interface types, e.g., silicone-based interfacing structures, gel-based interfacing structures. For example, the present technology may be retrofit or otherwise provided to existing masks, e.g., non-foam cushions.

One or more examples may include exemplary dimensions. Although specific dimensions and ranges may be provided, it is to be understood that these dimensions and ranges are merely exemplary and other dimensions and ranges are possible depending on application. For example, ranges that vary from those provided +/−10% may be suitable for particular applications.

Mask System

Figure 1:
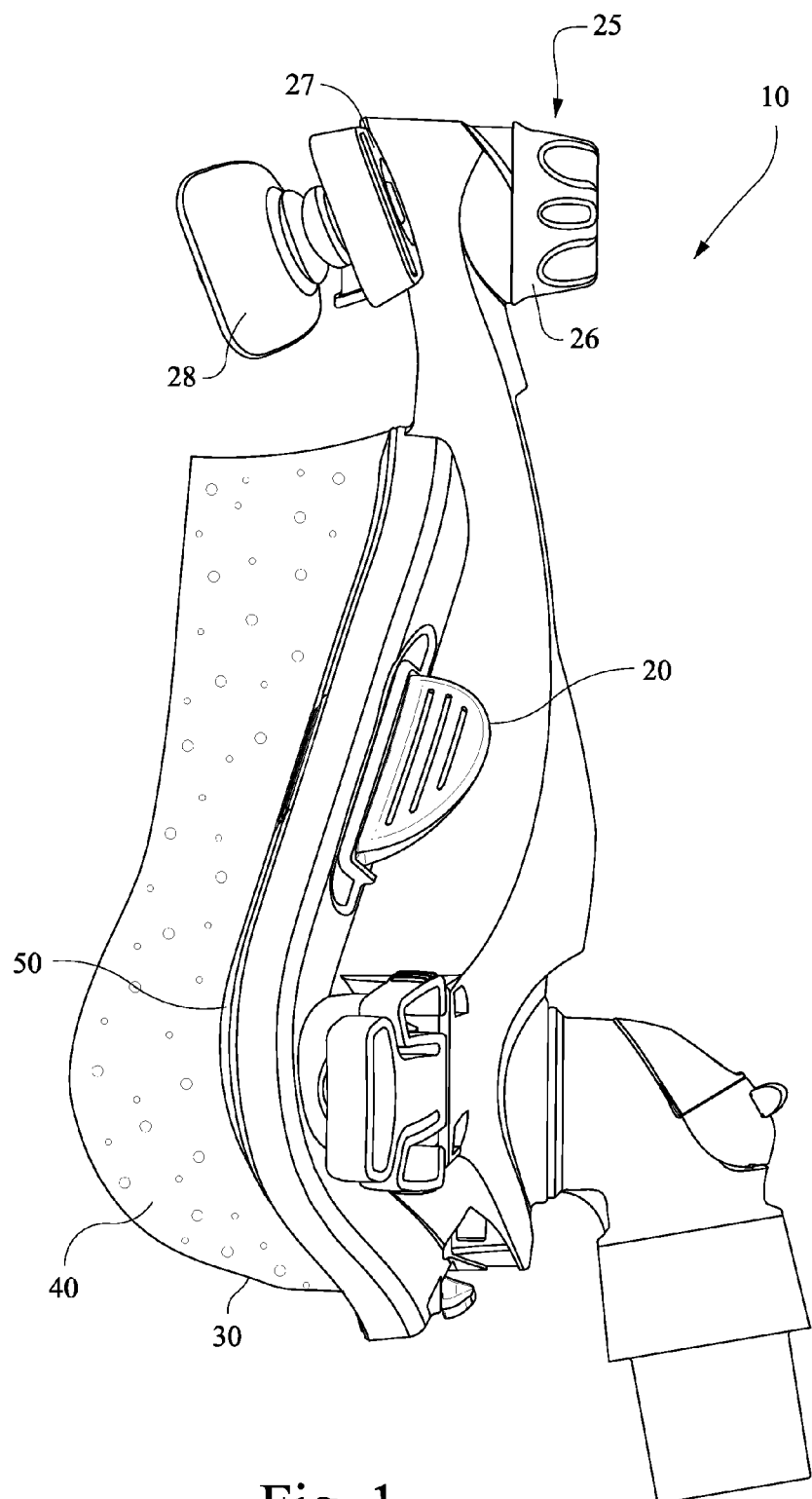
FIG. 1 is a side view of a mask system including a foam-based interfacing structure according to an example of the disclosed technology.
Figure 2:
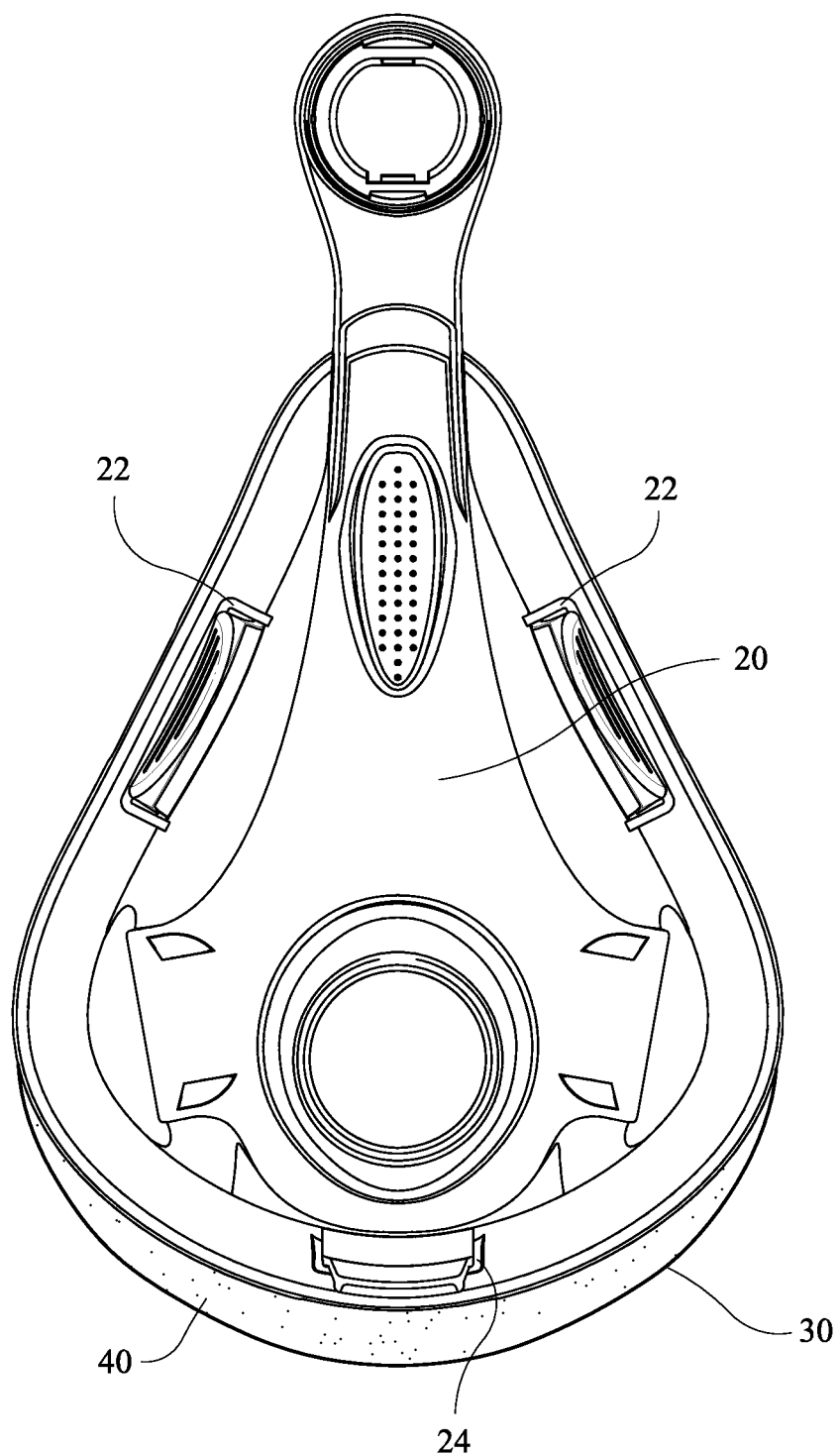
FIG. 2 is a front view of the mask system of FIG. 1.

FIGS. 1 and 2 show a full-face mask system 10 including a frame 20 and a foam-based interfacing structure 30 (e.g., cushion) provided to the frame and adapted to contact the patient's face. The full-face mask system is intended for use in positive pressure therapy for users with Obstructive Sleep Apnea (OSA) or another respiratory disorder.

While each example below is described as including a full-face interface type, aspects of the technology may be adapted for use with other suitable interface types, e.g., nasal interface, nozzles, nasal prongs, nasal cradle, etc.

Foam-Based Interfacing Structure

The foam-based interfacing structure 30 includes a foam cushioning component or cushion component 40 and a cushion-to-frame component 50 provided to the foam cushioning component 40. The cushioning component 40 is structured to contact the patient's face and the cushion-to-frame component 50 is structured to secure the interfacing structure to the mask frame 20.

In one form of the present technology, the foam cushioning component 40 is manufactured to have a relatively flat, two-dimensional surface on one side. Preferably, the cushioning component 40 extends in a length dimension and a width dimension.

Exemplary materials and properties for the foam cushioning component are provided in PCT Application Nos. PCT/AU2009/000262 and PCT/AU2009/001144.

Clip Component

FIGS. 3 to 14 illustrate a cushion-to-frame component 50 according to an example of the technology. As illustrated, the cushion-to-frame component 50 is in the form of a clip component of clip portion. The clip component is structured to facilitate assembly/disassembly of the interfacing structure to the mask frame, enhance clip retention, enhance cushion-to-frame seal, enhance durability, and/or facilitate manufacture.

Figure 7:
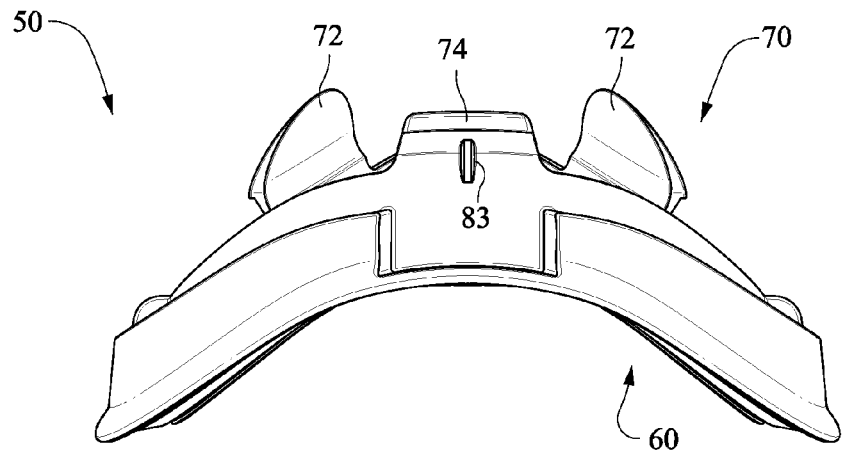
FIG. 7 is a bottom view of the cushion-to-frame component of FIG. 3.

In one preferred form, the cushion-to-frame component 50 has a curved, preferably three-dimensional shape that is complementary to a shape of a face of a person. Preferably, the cushion-to-frame component extends in a length dimension, a width dimension, and a depth dimension. See for example the cushion contacting side 60 of the cushion-to-frame component 50 in FIGS. 7, 8 and 9. For example, as shown in FIG. 7, the cushion-to-frame component has a shape that follows a chin region of a face. In one preferred form, the cushion-to-frame component 50 has different roll or bank angles in different regions of the cushion-to-frame component 50. The different roll or bank angle is, in one form, constructed to align the cushion contacting side 60 of the cushion-to-frame component 50 at an angle that is approximately orthogonal to the surface of the face, in at least some regions of the face, in use. In another form, the different roll or bank angle is constructed to align the cushion contacting side 60 of the cushion-to-frame component 50 at an angle that is not orthogonal to the surface of the face, for example, at an acute angle to the surface of the face in use.

Material

The cushion-to-frame component 50 may be constructed of a material having greater structural integrity than the foam cushioning component 40 so as to aid assembly of the cushioning component 40 to the frame 20. For example, the cushion-to-frame component 50 may be constructed of a material providing sufficient flexibility, strength, and processability, e.g., a material having the flexibility of rubber, strength of plastics, and processability of thermoplastics. In an example, the cushion-to-frame component 50 may be molded of TPE such as HYTREL®, e.g., specifically HYTREL® 5556 by DuPont™. However, the cushion-to-frame component 50 may be constructed of other suitable materials, e.g., harder, denser and/or lower permeability foam than the foam of the foam cushioning component (e.g., a foam having a density greater than 50 kg/m$^3$); nylon; polycarbonate; polypropylene; silicone (e.g., silicone having a hardness of at least 70 Shore A); cast or molded microcellular polyurethane foam.

In an example, the cushion-to-frame component 50 may be integrally formed in one piece with the cushioning component 40 but include different properties than the cushioning component, e.g., harder, denser and/or lower permeability foam than foam cushioning component.

Contour, Shape, and Size

The clip component 50 includes a cushion contacting side or cushion side 60 (e.g., see FIGS. 3 and 6) adapted to support or otherwise interface with the cushioning component 40 and a frame contacting side or frame side 70 (e.g., see FIGS. 4 and 5) adapted to engage or otherwise interface with the mask frame 20. The shape of the top surface of the cushion side may be used to correctly align and position the cushioning component with the patient's face, e.g., see WO 2010/028425. For example, the clip component may distort or orient the cushioning component into a particular shape. Since the clip component is relatively more rigid than the cushioning component, the cushioning component is forced to retain the shape or position of the clip component.

The general contour and shape of the frame contacting side may be configured to align with the frame to which it is attached. The general contour and shape of the cushion contacting side may be used to shape the cushion component, e.g., foam-based cushioning component sufficiently compliant so it will adapt to the shape of the cushion contacting side when secured thereto.

Also, the clip component may be provided in alternative sizes corresponding to alternative size cushions, e.g., small, medium, large, etc. Alternatively, a single size clip component may be structured to support alternative size cushions. In another example, different clips may be manufactured to customize the shape of a cushion for individual user anthropometrics, sizing, and/or other purposes. Possibly, a single, common size frame and a single, common size cushion may be used. Alternatively, various frames, clips, and cushions may be made and various combinations may be used to customize the size and fit. If the cushion is not permanently attached to the clip, e.g., silicone cushion, it may be interchangeable. If the cushion is permanently attached to the clip, e.g., foam cushion, several different clip and cushion combination assemblies may be manufactured.

Frame Contacting Side

The frame contacting side 70 includes a pair of side clip portions 72 on respective sides of the component and a bottom or lower clip portion 74 adapted to engage respective slots provided on the mask frame (e.g., see side slots 22 and bottom slot 24 in frame 20 in FIG. 2). It should be appreciated that the frame contacting side may have any suitable number of clip portions, and the number of slots in the mask frame may be varied according to the number of clip portions.

In the illustrated example, the side clip portions include a different structure or configuration than the bottom clip portion. However, it should be appreciated that the clip portions may have other suitable arrangements, e.g., bottom clip portion similar structure to side clip portions.

Side Clip Portions

As illustrated, each side clip portion 72 extends from an inner wall 52 of the cushion-to-frame component 50. Each side clip portion 72 is relatively thick and defines a shoulder 73 adapted to engage an edge of the corresponding frame slot. Each side clip portion 72 includes contoured finger grips 75 (e.g., see FIG. 12) to facilitate assembly. In addition, one or more recesses or cut-outs 77 (e.g., three recesses as shown in FIGS. 3, 4, 8, 10, 11, and 12) are provided to a base portion 76 adjacent each side clip portion. As illustrated, each base portion 76 extends between the inner wall 52 and an outer wall 54 of the component adjacent a respective side clip portion. Such recesses also enhance grip of the component to facilitate assembly. In an example, one or more ribs may be provided within the recesses or cut-outs 77, e.g., to increase the stiffness of the clip to enhance feedback during assembly/disassembly.

Ribs

Figure 8:
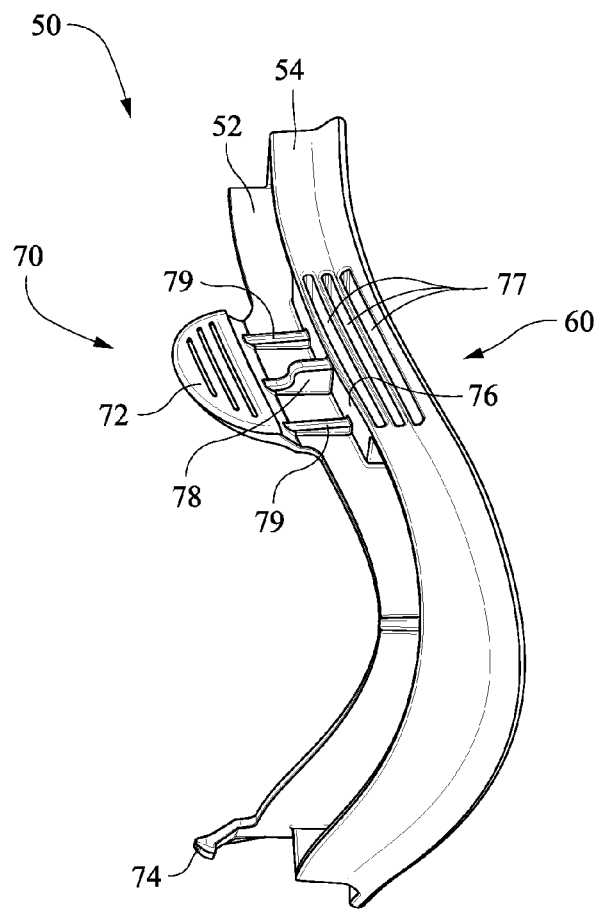
FIG. 8 is a side view of the cushion-to-frame component of FIG. 3.
Figure 12:
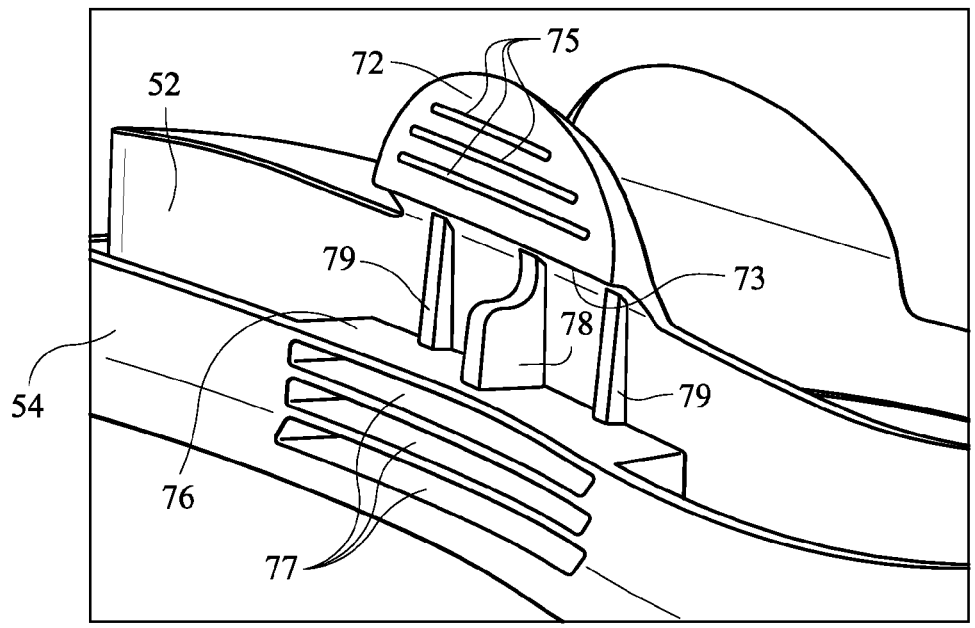
FIG. 12 is an enlarged perspective view of a side clip portion of the cushion-to-frame component of FIG. 3.
Figure 13:
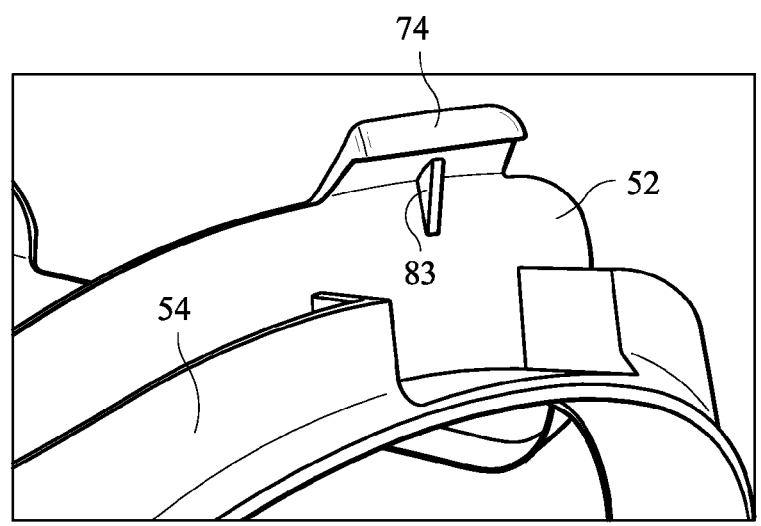
FIG. 13 is an enlarged perspective view of a bottom clip portion of the cushion-to-frame component of FIG. 3.

Also, as best shown in FIGS. 8 and 12, a central rib 78 and side ribs 79 are provided to the inner wall 52 between each side clip portion 72 and the base portion 76. As illustrated, the central rib 78 is contoured along its length and protrudes further outwardly from the inner wall 52 than the side ribs 79. However, other suitable rib configurations are possible. In use, the ribs are structured and arranged to control the flexibility of the side clip portion 72, e.g., to increase stiffness and therefore enhance retention.

In addition to the base portions 76, one or more additional ribs 85 (e.g., see FIG. 4) are provided between the inner and outer walls 52, 54, e.g., to enhance rigidity. Ribs 85 may also assist to align the clip to the frame, so that the clip wall does not incorrectly jam with the frame wall. That is, the ribs 85 are structured to prevent "hang up" of the clip on the frame, i.e., ribs aid insertion by preventing misalignment of the clip to the frame.

Reinforcement of Frame Seal

In an example, the side clip portions 72 may be configured such that the side clip portions are squeezed or forced towards one another when engaged with respective slots 22 of the mask frame 20. Also, the ribs 78 provided adjacent each clip portion 72 engage the frame and enhance the force at which the sealing lip adjacent the side clip portions engage the frame, so as to reinforce the seal at these opposite sides of the component. That is, the seal is reinforced along a generally concave or pear-shaped portion of the component.

Bottom Clip Portion

Figure 19:
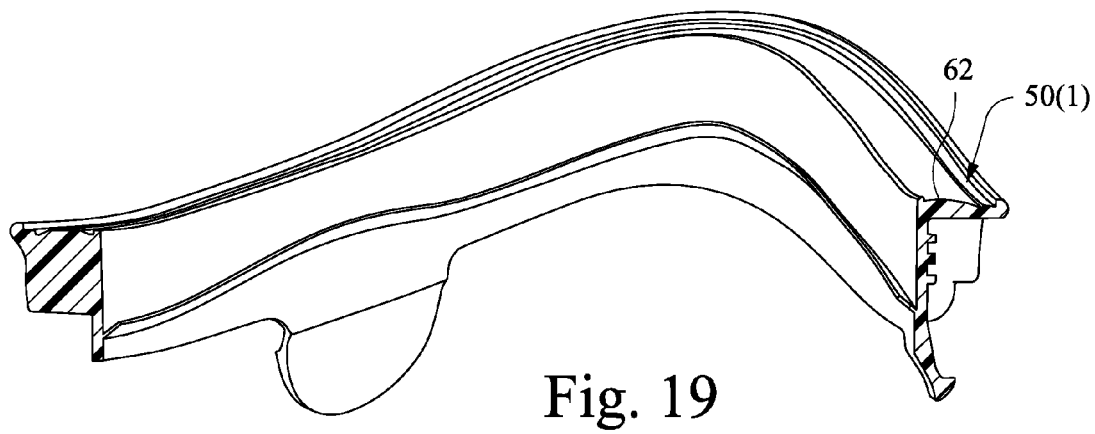
FIG. 19 is a cross-sectional view of a cushion-to-frame component in a chin region according to an example of the disclosed technology.
Figure 21:
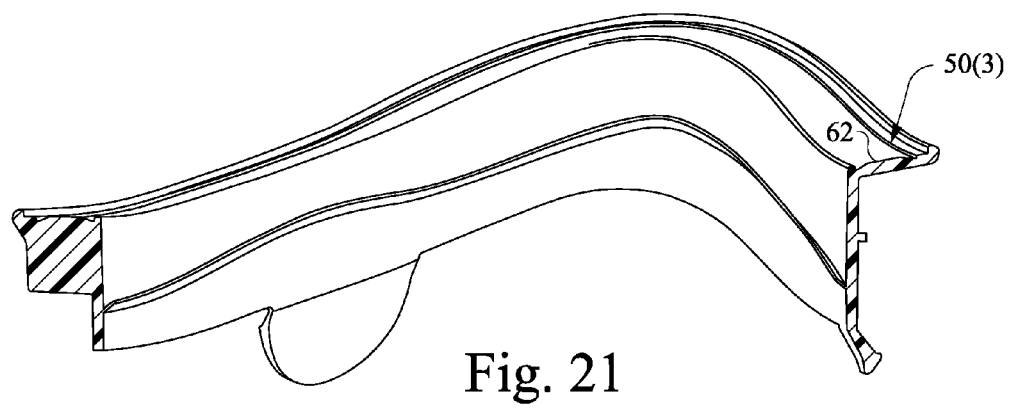
FIG. 21 is a cross-sectional view of a cushion-to-frame component in a chin region according to another example of the disclosed technology.
Figure 22:
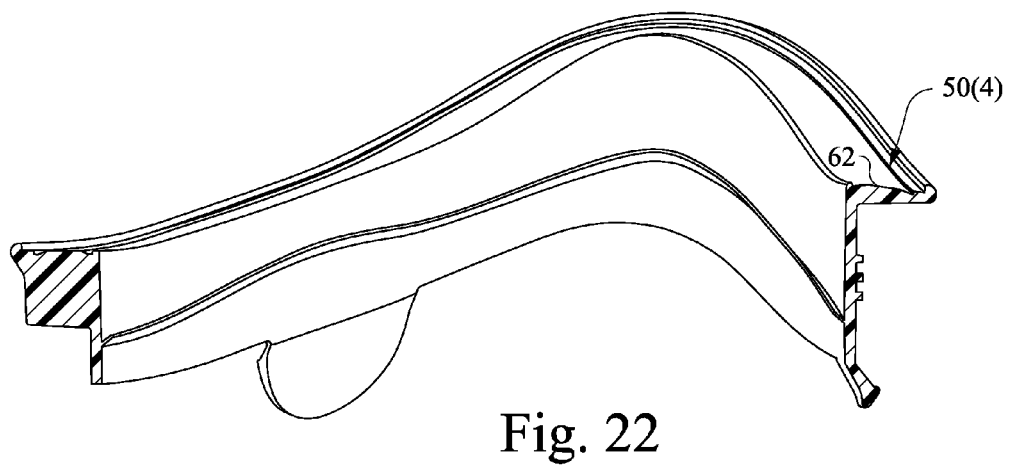
FIG. 22 is a cross-sectional view of a cushion-to-frame component in a chin region according to another example of the disclosed technology.

The bottom clip portion 74 has a lower profile than the side clip portions and does not provide finger grips. The bottom clip portion 74 extends from the inner wall 52 and defines a shoulder 81 (e.g., FIG. 14) adapted to engage an edge of the corresponding frame slot. A rib 83 (e.g., see FIGS. 7, 13 and 14) is provided to the inner wall 52 adjacent the bottom clip portion 74 to control the flexibility of the bottom clip portion 74, e.g., to increase stiffness and therefore enhance retention. As illustrated, the rib is tapered along its length, however other suitable rib configurations are possible. Also, more than one rib may be provided adjacent the bottom clip portion 74, e.g., to provide additional support, as shown in FIGS. 19, 21, and 22 for example.

Figure 9:
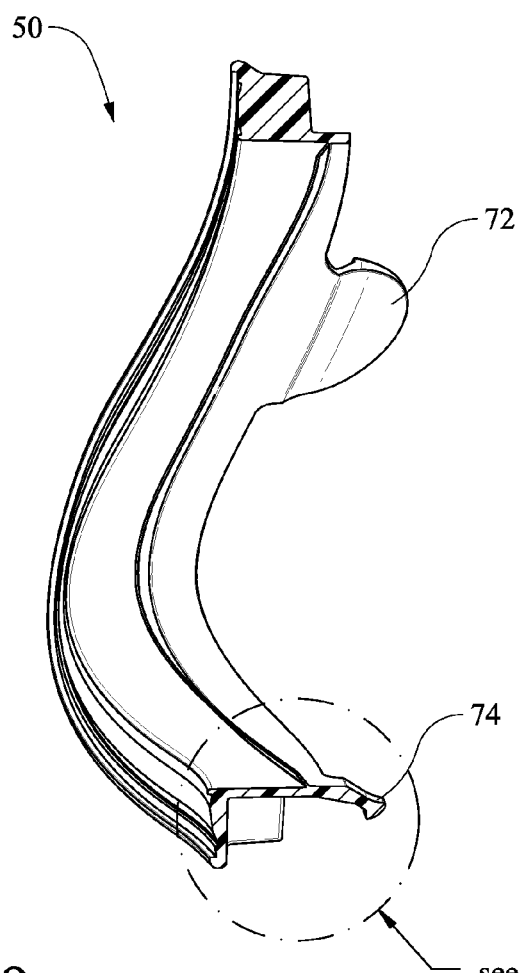
FIG. 9 is a cross-sectional view through line 9-9 of FIG. 5.
Figure 9A:
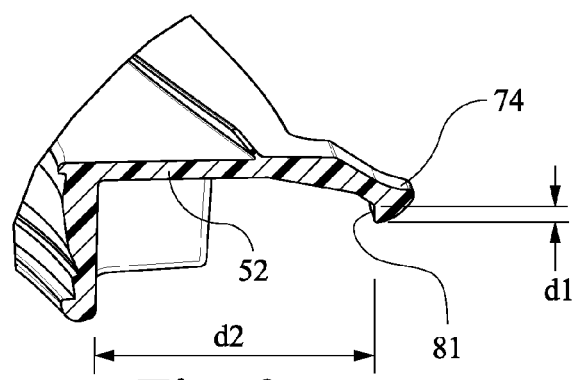
FIG. 9a is an enlarged view of a portion of FIG. 9.
Figure 14:
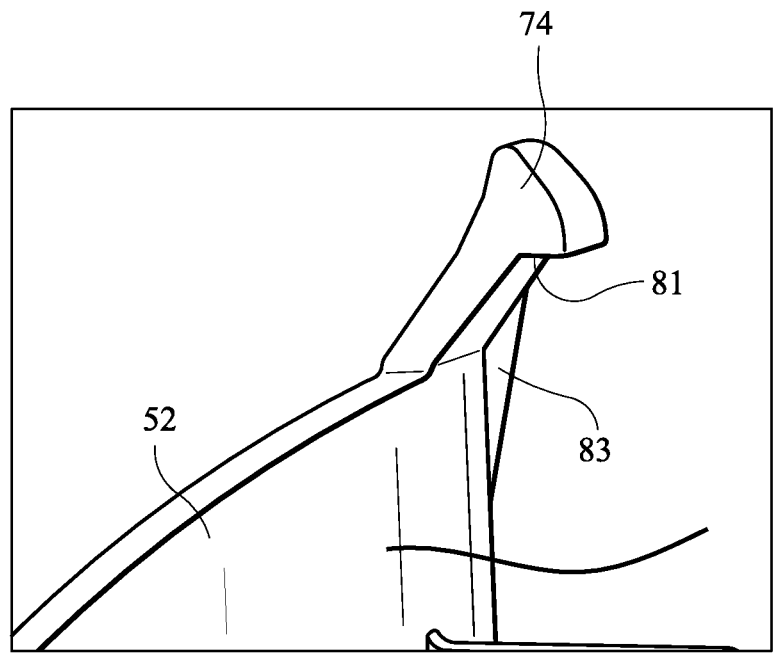
FIG. 14 is another enlarged perspective view of a bottom clip portion of the cushion-to-frame component of FIG. 3.

As shown in FIG. 14, the bulbous free end of the bottom clip portion 74 has been thickened to enlarge the surface area or snap engagement length provided by the shoulder 81 adapted to engage an edge of the corresponding frame slot, e.g., to enhance retention. As shown in FIG. 9a, the shoulder 81 may have a length d1 of about 1-3 mm, e.g., about 2 mm, about 1.8 mm. Also, d2 in FIG. 9a may be about 18-22 mm, e.g., about 20 mm. However, it should be appreciated that other suitable dimensions are possible, e.g., depending on interface type.

Sealing Lip

A sealing lip 90 extends along the perimeter of the inner wall 52 towards the interior of the component. In use, the sealing lip 90 is adapted engage an inner wall of the mask frame and provide a seal, e.g., prevent leak between the mask frame and the cushion-to-frame component. As shown in FIG. 10, a lower surface 52(1) of the inner wall is offset outwards from an upper surface 52(2) of the inner wall to increase the length of the sealing lip. Also, the sealing lip is suitably angled to allow folding of the lip towards the inner wall in use.

Progressive Engagement of Sealing Lip

In an example, the sealing lip may be structured to progressively engage the frame, i.e., sealing lip configured to engage the frame in steps. For example, the length of travel of the sealing lip on the frame may be modified by adjusting the position of the sealing lip's height on the side wall. Also, the length of the sealing lip may be varied around the perimeter of the component, e.g., sealing lip longer on the sides of the component. In addition, the angle of the sealing lip with respect to the inner wall may be varied. The angle and/or length of the sealing lip may enhance seal and/or control ease of insertion or assembly.

Exemplary Dimensions

FIGS. 10 and 11 show exemplary dimensions according to an example of the technology. For example, as shown in FIG. 10, d1 is about 2 to 2.5 mm (e.g., 2.2 mm), d2 is about 1.8 to 2.3 mm (e.g., 2.0 mm), t is about 0.25 to 0.45 mm (e.g., 0.35 mm), R is about 0.05 to 0.25 mm (e.g., 0.1 mm), and a is about 40-60°, e.g., 51°. In FIG. 11, d3 may be about 11-12 mm, e.g., 11.5 mm. In an example, the wall thickness of the clip component may be about 1.3-1.5 mm. Although specific dimensions are indicated, it is to be understood that these dimensions are merely exemplary and other dimensions are possible depending on application.

In an alternative example, the internal radius of the sealing lip (e.g., identified by dimension R in FIG. 10) may be replaced with a sharp internal edge.

Cushion Contacting Side

As best shown in FIGS. 3, 6, 9a, 10, 11 and 11a, the cushion contacting side 60 provides a platform 62 adapted to engage and support at least a portion of the cushioning component 40. The cushioning component may be attached to the cushion contacting side 60 in any suitable manner, e.g., adhesive, insert molding, mechanical interlock, etc. Exemplary adhesives include cyanoacrylate (e.g., Loctite®), polyurethane hot melt glue, polyurethane, and other suitable adhesives structured to prevent detachment and brittleness.

Preferably, the cushioning component 40 is relatively soft and flexible compared to the cushion-to-frame component 50, and thus when assembled, the cushioning component 40 adopts a shape that is imparted by the cushion-to-frame component 50. This arrangement can simplify a manufacturing process, and enable the construction of an interfacing structure that more closely matches a seal-forming portion adapted to engage the patient's face. For example, in one preferred form, the cushioning component 40 can be manufactured to have a two-dimensional shape, and subsequently held by the cushion-to-frame component in a three-dimensional shape that is complementary to the corresponding portion of the patient's face. For example, the cushioning component 40 can be arranged at least in some regions to be aligned to make an angle with the surface of the face, rather than being orthogonal to the face.

That is, the cushioning component 40 may be manufactured to have a relatively flat, two-dimensional shape, e.g., the cushioning component includes a surface on one side that extends in a length dimension and a width dimension. When the cushioning component 40 is attached to the cushion-to-frame component 50, the cushion-to-frame component 50 is constructed and arranged to impart a three-dimensional shape to the two-dimensional cushion component, i.e., add a depth dimension to the cushioning component to match the curvature of the user's face. It should be appreciated that the cushion-to-frame component may be structured to provide alternative curvatures along its perimeter (e.g., different roll or bank angles in different regions of the cushion-to-frame component) in order to adjust the shape or angle, e.g., depth dimension, imparted to different regions of the cushioning component. For example, the cushion-to-frame component may be structured to impart different shapes or angles, e.g., different depths, to the cushioning component in the nose bridge region with respect to the chin region. In one example, the cushion-to-frame component may be structured to twist the cushioning component about its longitudinal axis.

Platform

In the illustrated example, the platform 62 provides an engagement surface 64 adapted to engage the cushioning component and to form the cushion component into the shape and position for an effective (e.g., comfortable and sealed) patient interface. Inner and/or outer flanges or lips 66, 68 may be provided to opposing ends of the platform to help guide, support and/or retain the cushioning component on the platform 62 and/or to cover the joint of the cushioning component and the adhesive. For example, the flanges may define a nest for the cushioning component within the platform to help reduce misalignment between the clip component and the cushioning component. Also, the flanges may prevent overflow, e.g., of adhesive during assembly of the cushioning component, over ends of the platform. In addition, the flanges may provide a guide to aid manufacturing alignment. The flanges may also help with cushion blow-out and/or biasing cushion wall to roll.

In an example, the engagement surface 64 may be considered a "channel" or "glue channel" cut into the cushion contacting side 60 to permit the passage of glue and capture excess glue. For example, the generally triangular-shaped channels 65(1), 65(2) provide glue tracks to receive excess glue. It should be appreciated that the channels 65(1), 65(2) may have other suitable widths, depths, shapes, and/or positions. The inner flange 66 may be provided as a result of cutting or otherwise forming the inner glue channel 65(1). The relatively flat shelf 67 adjacent the outer flange 68 provides a "flange" for the outer glue channel 65(2). The outer flange 68 is in the form of a cushion guide lip to provide an alignment feature when positioning and locating the cushioning component during the gluing process. In addition, the outer flange 68 hides the edge of the cushioning component so as to hide the glue joint which could appear untidy. However, it should be appreciated that the channels and flanges may be optional features, e.g., depending on the assembly method and/or adhesive.

As best shown in FIG. 11a, the engagement surface 64 includes a non-linear portion along its width, e.g., including incline portions, decline portions, flat portions, etc. However, it should be appreciated that the engagement surface may be relatively flat. The non-linear or uneven engagement surface may be help to shape the cushioning component and/or retain the cushioning component on the platform. For example, the non-linear portion of the engagement surface may positively locate the cushioning component, provide larger surface area for retention, and/or define one or more notches to define stop or retaining surfaces.

Assembly

In use, the clip component is attached or otherwise secured to the cushioning component to establish the interfacing structure, and then the interfacing structure is engaged with the mask frame by inserting the clip portions of the clip component into respective slots of the mask frame, e.g., with a snap-fit. The clip portions may each provide an audible click, which provides audible and tactile feedback regarding a proper connection.

In addition, the clip portions are structured to reduce the assembly and disassembly forces. For example, assembly force may be less than 75N, e.g., 60-70N, 60-65N, e.g., about 65N. Disassembly force may be less than 17N, e.g., 10-15N, 11-14N, about 13N. Although specific forces are indicated, it is to be understood that these forces are merely exemplary and other forces are possible depending on application, e.g., interface type. Also, the clip portions may be tuned to desired assembly/disassembly forces.

Structure to Prevent Foam in the Eyes

Figure 15:
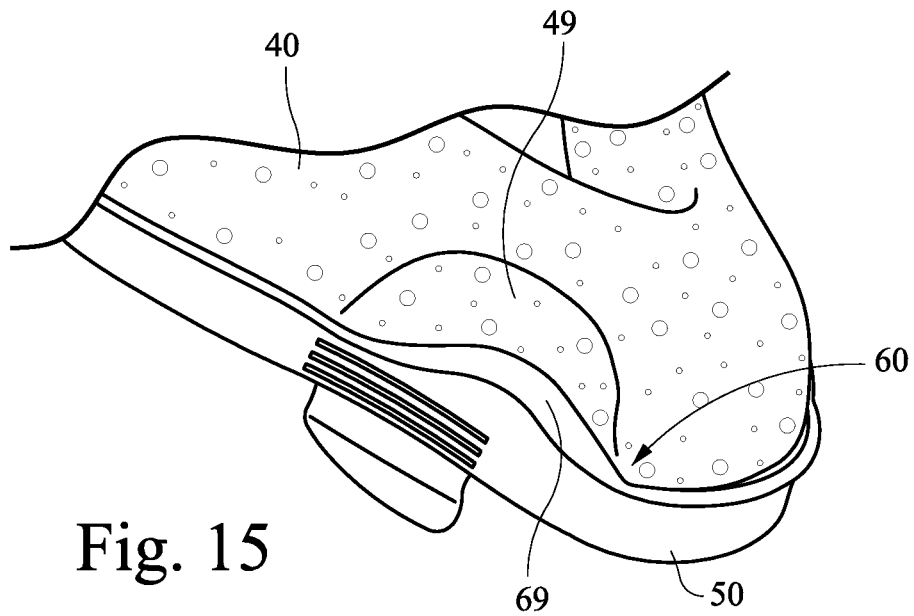
FIG. 15 is a partial perspective view of a cushion-to-frame component and a foam-based interfacing structure according to an example of the disclosed technology.
Figure 16:
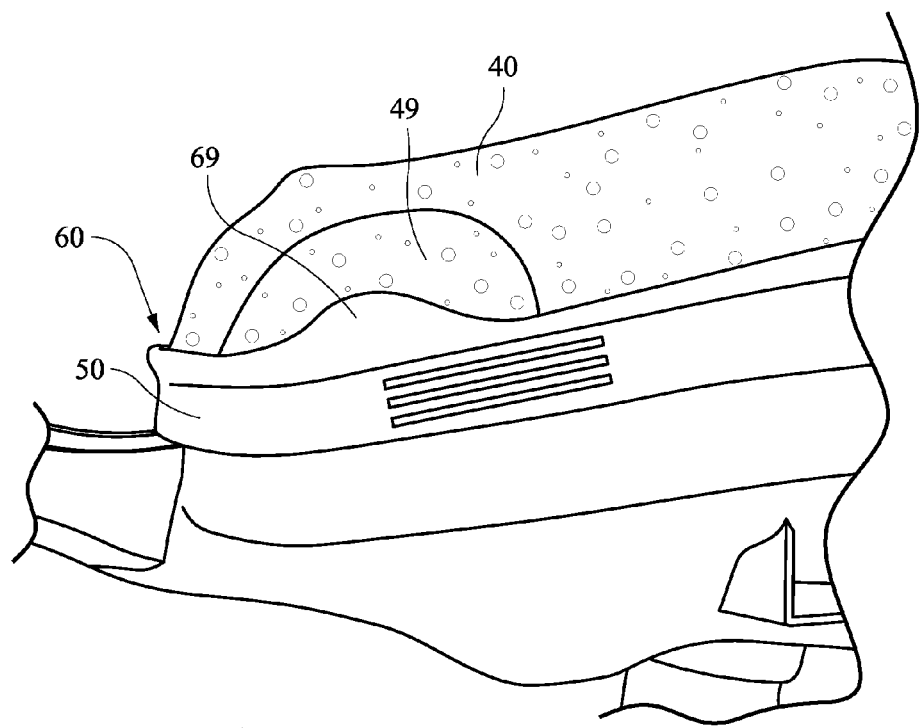
FIG. 16 is another partial perspective view of the cushion-to-frame component and the foam-based interfacing structure of FIG. 15.

In an example, as shown in FIGS. 15 and 16, arcuate-shaped protrusions or wings 69 may be provided to respective sides of the cushion contacting side 60 of the clip component 50 adjacent side of nose regions of the foam cushioning component 40. Such protrusions or wings are positioned proximal to the patient's eyes in use so as to hold the foam cushioning component away from the patient's eyes.

Also, as shown in FIGS. 15 and 16, the foam cushioning component 40 may include scalloped or inwardly curved surfaces 49 in these side-of-nose regions (e.g., adjacent respective protrusions 69) to reduce the amount of foam near the patient's eyes.

Figure 17:
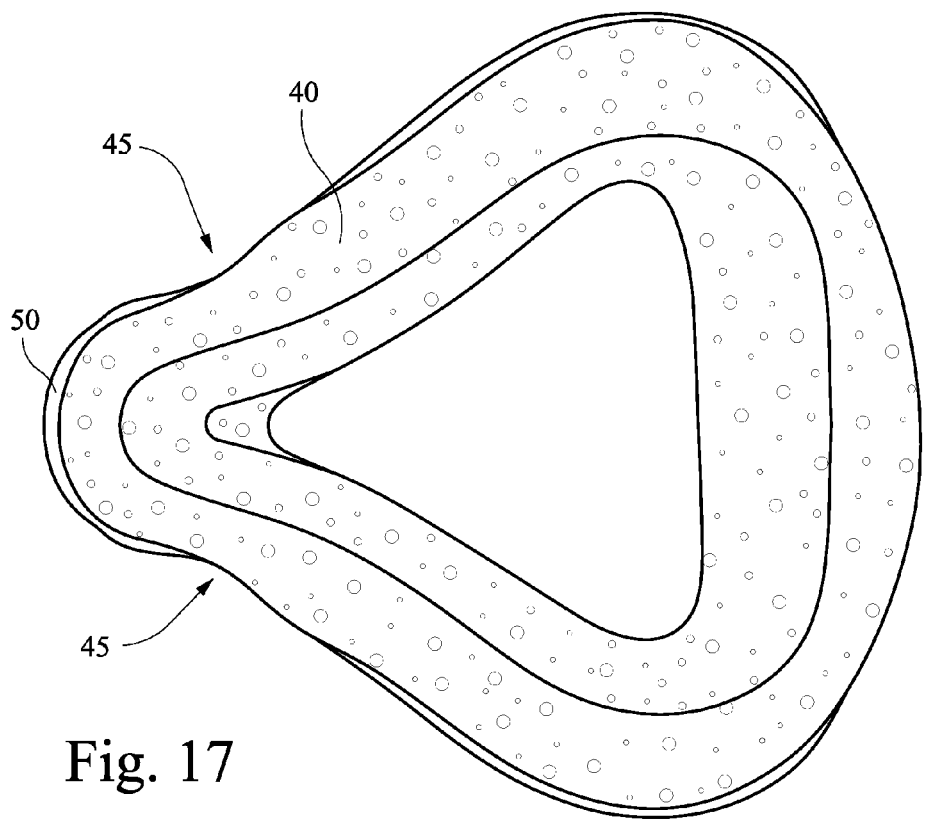
FIG. 17 is a top view of a cushion-to-frame component and a foam-based interfacing structure according to an example of the disclosed technology.

In addition, as shown in FIG. 17, the clip component 50 and cushioning component 40 attached thereto may include a scooped or inwardly curved portion 45 in the side of nose region so that the cushioning component is positioned away from the patient's eyes in use.

Figure 3:
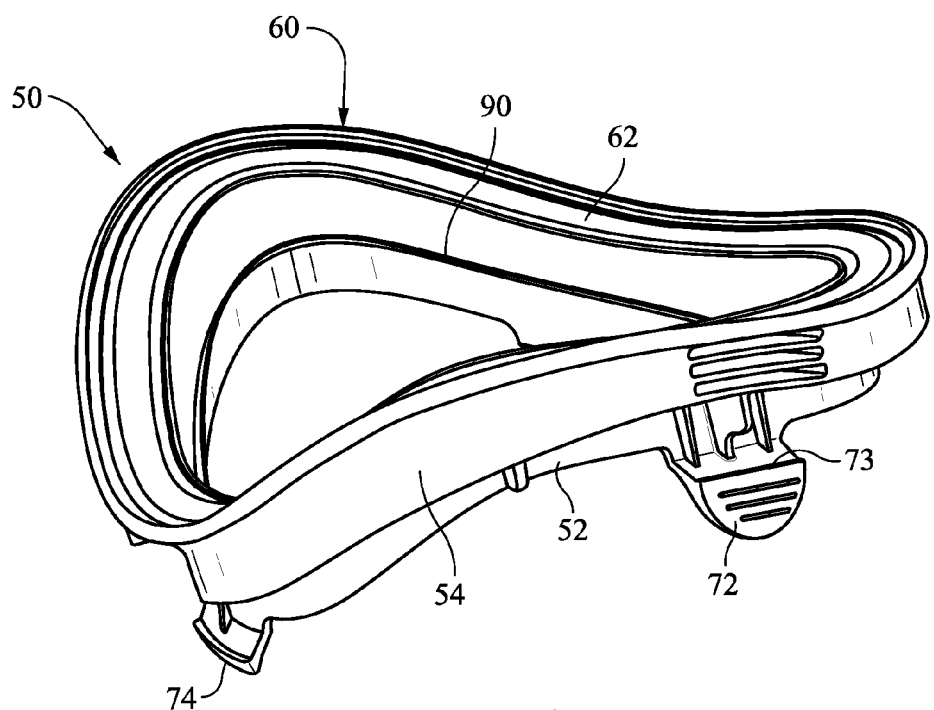
FIG. 3 is a perspective view of a cushion-to-frame component for a foam-based interfacing structure according to an example of the disclosed technology.
Figures 1, 18:
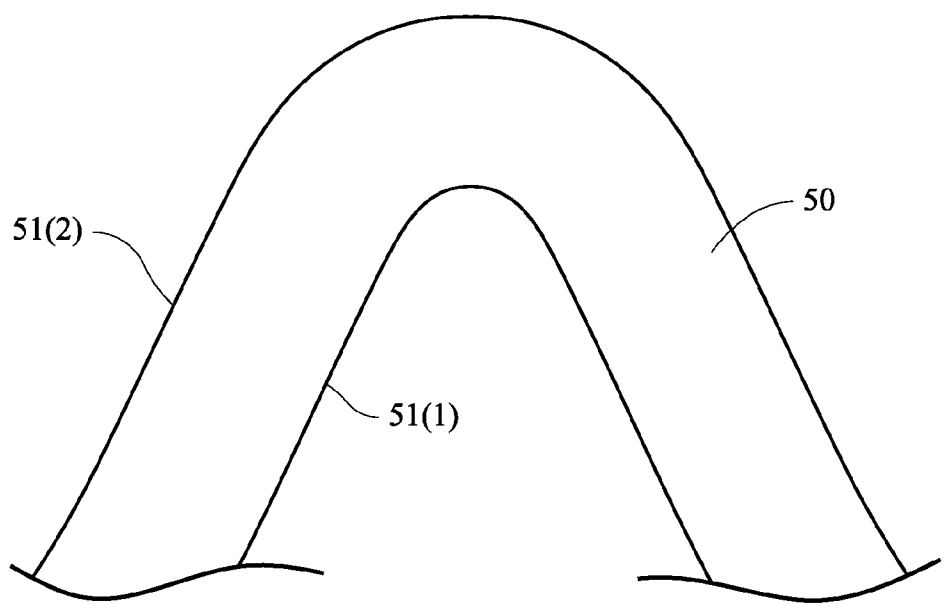
Figures 2, 18:
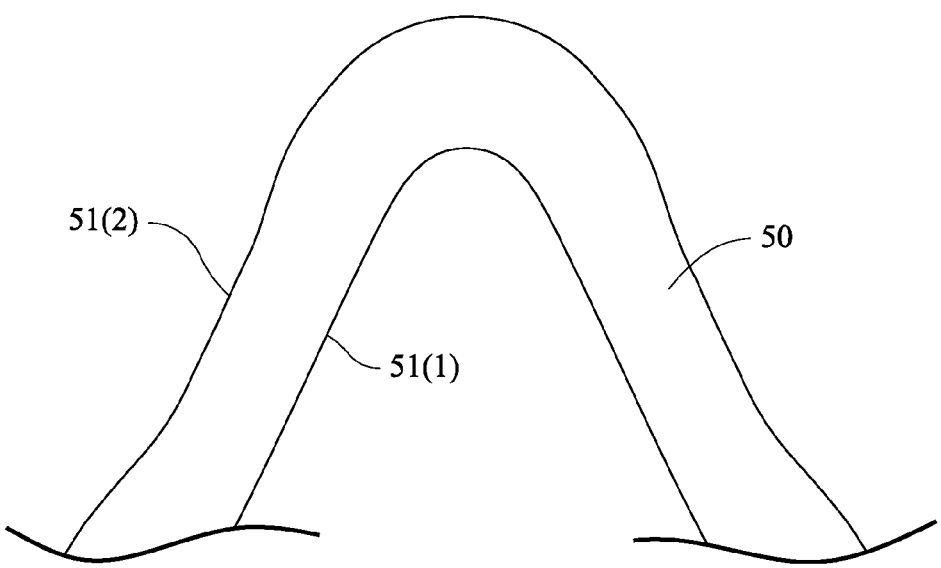
Figures 3, 18:
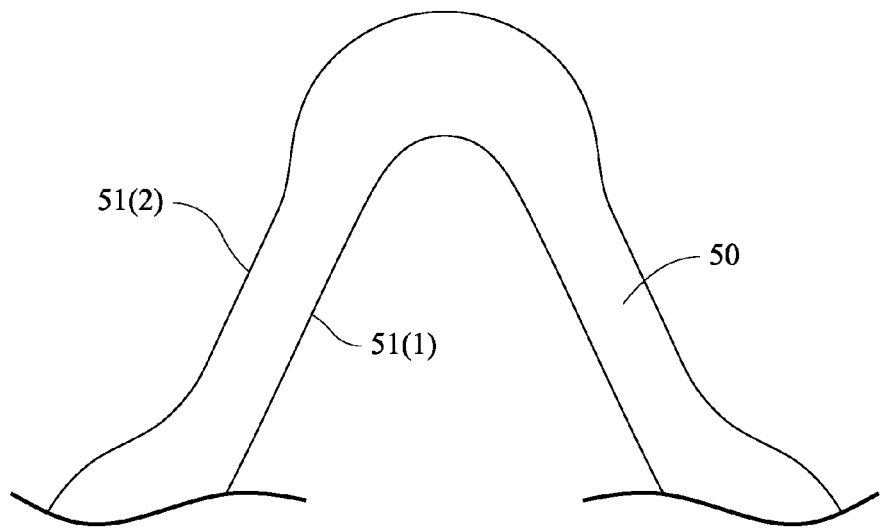

FIGS. 18-1 to 18-3 schematically show clip components according to alternative examples of the disclosed technology. FIG. 18-1 shows an example in which the inner and outer edges 51(1), 51(2) of the clip component 50 are generally parallel. In FIG. 18-2, the outer edge 51(2) is scooped or curved inwards in the side of nose regions. FIG.

18-3 is similar to FIG. 18-2 but with the outer edge 51(2) curved more inwardly in the side of nose regions.

Structure to Fit More Chin Shapes

In an example, the clip component may be shaped or structured at the chin region to fit more patients. For example, the clip component may be structured to decrease the amount of foam that would go in the eye and/or improve seal and comfort at the lower mouth.

Figure 20:
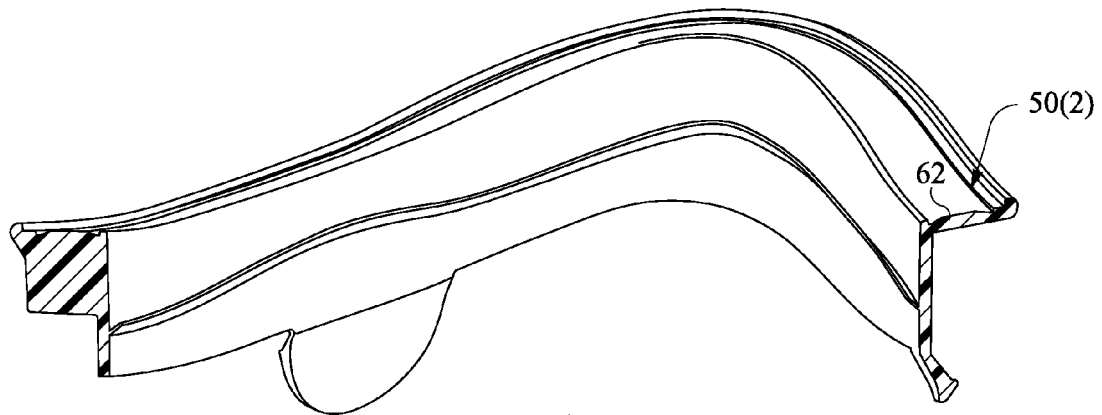
FIG. 20 is a cross-sectional view of a cushion-to-frame component in a chin region according to another example of the disclosed technology.

FIGS. 19 to 22 show cross-sections of clip components in a chin region according to alternative examples of the disclosed technology. In FIG. 19, the clip component 50(1) includes a cross-sectional configuration similar to the clip component 50 described above. In FIG. 20, the clip component 50(2) provides a platform 62 at the chin region that is sloped generally inwards, e.g., compared to that of FIG. 19. In FIG. 21, the clip component 50(3) provides a platform 62 at the chin region that is raised and sloped generally inwards, e.g., compared to that of FIG. 19. In FIG. 22, the clip component 50(4) provides a platform 62 that is raised from the cheek region down to the chin region.

Forehead Support Pad

In the illustrated example, as shown in FIG. 1, a forehead support 25 is provided to the mask frame 20 to provide a support and stability mechanism between the mask system and the patient's forehead in use. As illustrated, the forehead support 25 includes an adjustment knob or dial 26 that is rotatable to extend or retract a forehead support plate 27 that carries one or more forehead support pads or cushions 28, e.g., constructed of an elastomeric material (e.g., silicone). Further details and examples of such forehead support are disclosed in PCT Publication No. WO 2006/074517, which is incorporated herein by reference in its entirety.

In an alternative example, the one or more forehead support pads may be at least partially constructed of foam (e.g., die cut foam or compression cut foam) or other conformable or compliant material, e.g., gel, fabric. Preferably, the conformable forehead support pad may be removably attachable to the forehead support, e.g., to allow for replacement.

Figure 23:
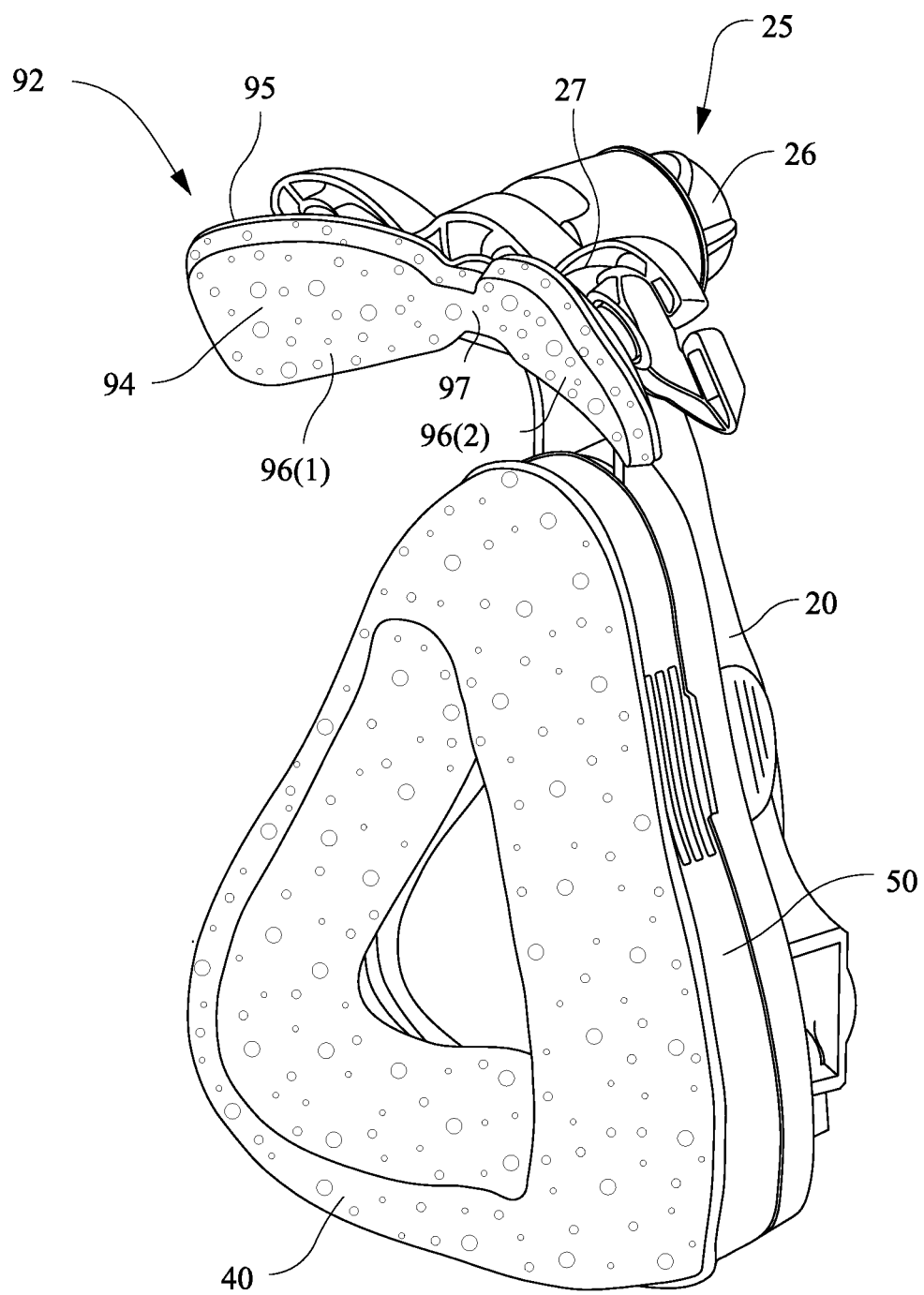
FIG. 23 is a perspective view of a mask system including a foam-based interfacing structure and foam-based forehead support pad according to an example of the disclosed technology.
Figure 24:
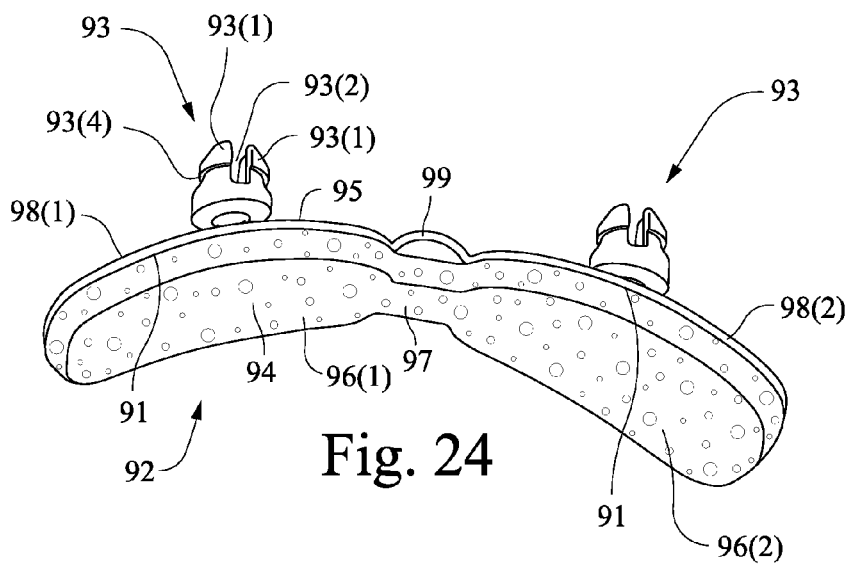
FIG. 24 is a perspective view of a foam-based forehead support pad according to an example of the disclosed technology.

FIGS. 23 and 24 show a forehead support pad 92 according to an example of the disclosed technology. As illustrated, the forehead support pad 92 includes a conformable cushioning component 94 structured to contact the patient's forehead and an attachment component 95 provided to the cushioning component and structured to secure the forehead support pad to the forehead support plate of the forehead support.

The attachment component 95 is constructed of a material (e.g., molded of plastic, nylon, etc.) having greater hardness or structural integrity than the conformable cushioning component (e.g., foam) so as to aid assembly of the conformable cushioning component to the forehead support plate 27.

The cushioning component 94 may be attached to attachment component 95 in any suitable manner. For example, the cushioning component may be adhesive backed or glued to the attachment component. In another example, the cushioning component may be co-molded to the attachment component.

In the illustrated example, the cushioning component 94 includes a pair of pads 96(1), 96(2) that are joined to one another by a bridge portion 97.

The attachment component 95 includes a pair of pad support portions 98(1), 98(2) that are joined to one another by a bridge portion 99. Each pad support portion 98(1), 98(2) includes a first side providing a surface 91 adapted to engage and support a respective pad 96(1), 96(2) of the cushioning component. The surface may be contoured to help shape the cushioning component, e.g., general concave contour to conform to patient's forehead profile. A second or opposite side of each pad support portion 98(1), 98(2) includes an attachment head 93 to attach the forehead support pad to the forehead support plate.

The bridge portion 99 is generally bowed or curved to allow flexibility between the pair of pad support portions 98(1), 98(2), and hence allow flexibility between the pair of pads 96(1), 96(2).

As illustrated, the attachment head 93 protrudes rearwardly from the pad support portion and adapted to be inserted into and interlock with a respective aperture formed in the forehead support plate 27, e.g., with a snap fit.

For example, as shown in FIG. 24, each attachment head 93 includes two legs 93(1) separated by a space 93(2) that provides a clip feature for snap-fit retention. The free end of each leg 93(1) is tapered to allow receipt of the legs into a respective aperture in the forehead support plate. The space or gap 93(2) between the legs allows the legs to flex inwardly when inserted into the respective aperture. A recessed portion is provided to each leg which provides a shoulder or retaining feature 93(4) for interlocking with the forehead support plate when the attachment head reaches it operative position and the legs resiliently return to original form.

The attachment component may have other suitable structures or geometries. In an example, the attachment between the attachment head and the pad support portion may be structured to enhance gimballing or flexibility.

Figure 4:
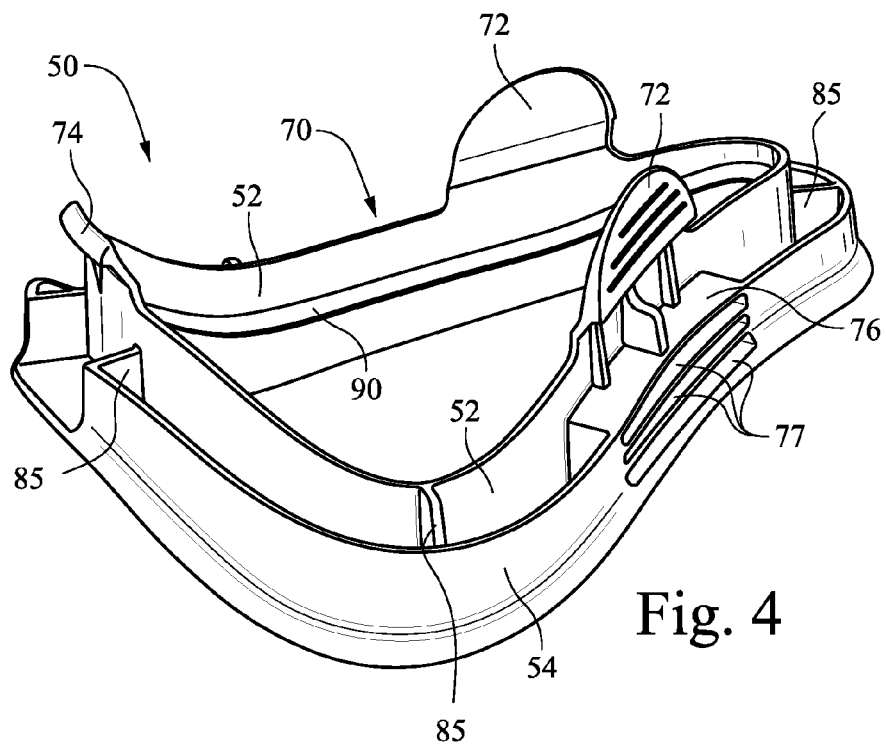
FIG. 4 is another perspective view of the cushion-to-frame component of FIG. 3.
Figure 5:
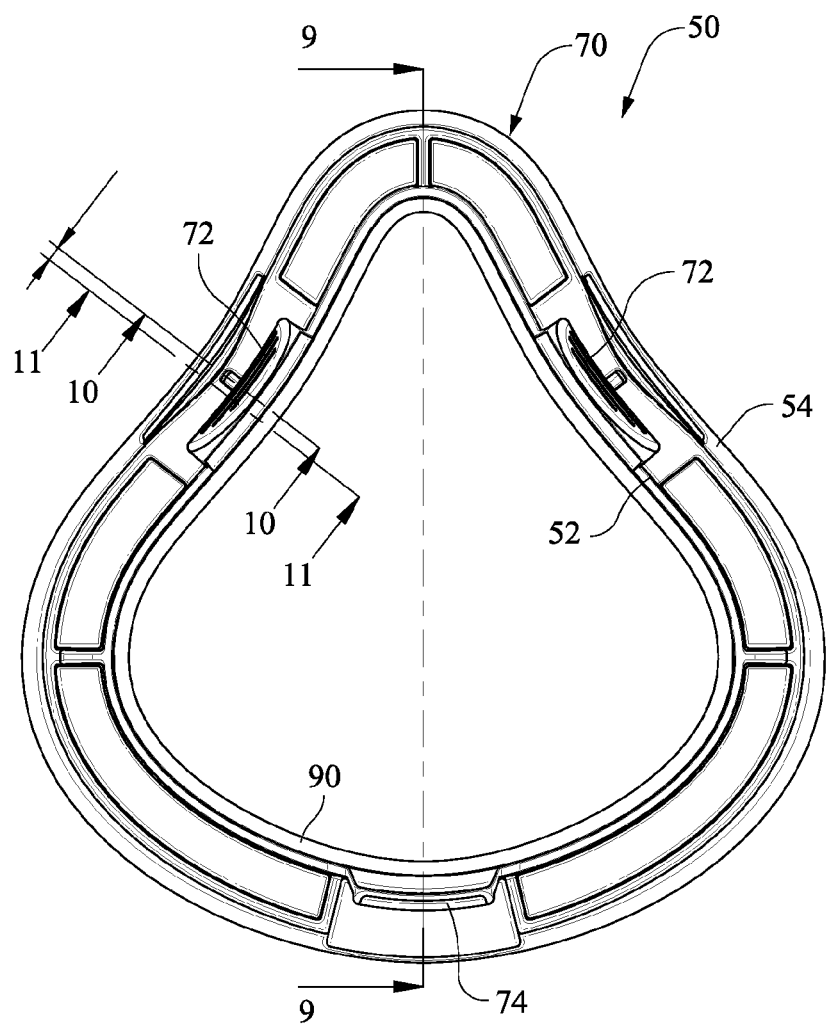
FIG. 5 is a plan view of a frame contacting side of the cushion-to-frame component of FIG. 3.
Figure 6:
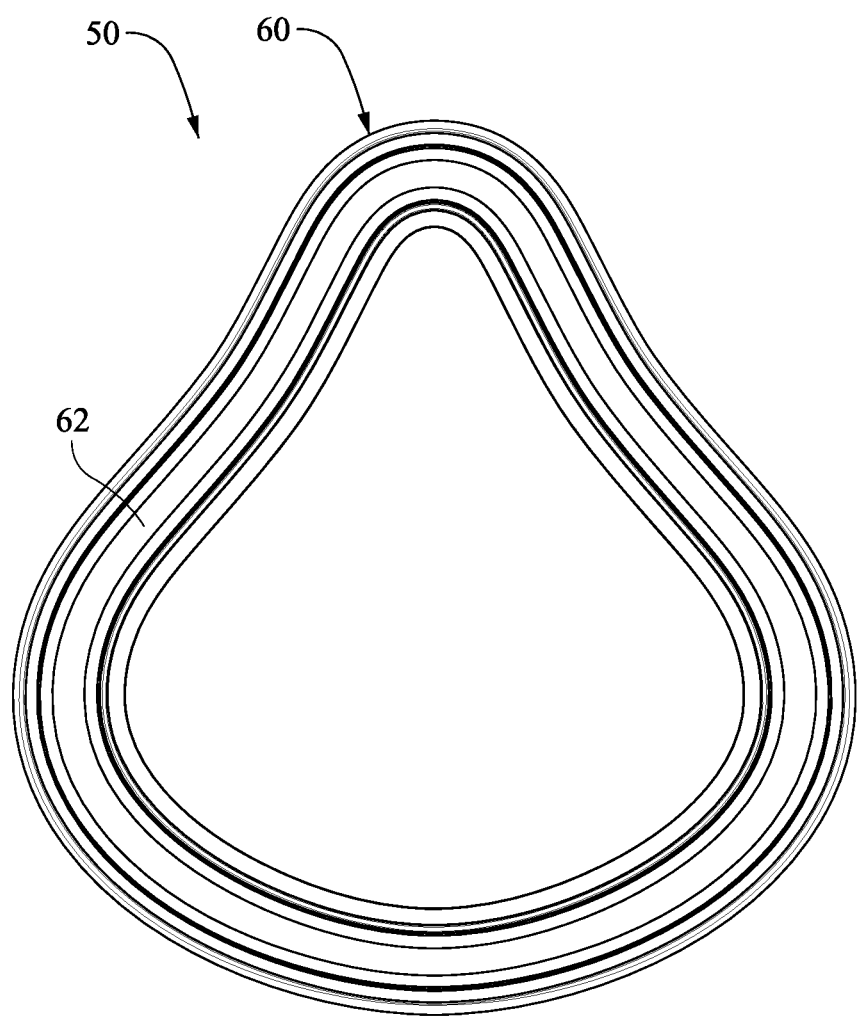
FIG. 6 is a plan view of a cushion contacting side of the cushion-to-frame component of FIG. 3.
Figures 1, 25:
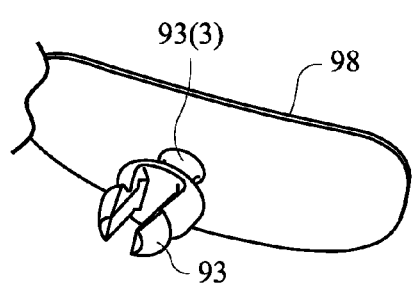
Figures 2, 25:
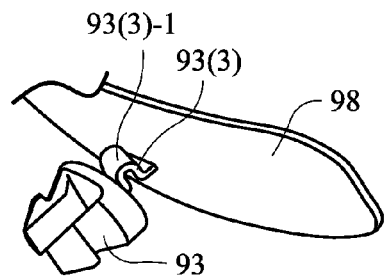
Figures 3, 25:
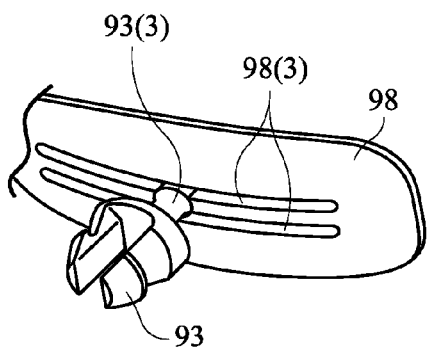
Figures 4, 25:
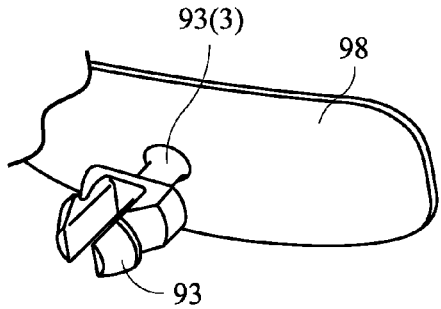
Figures 5, 25:
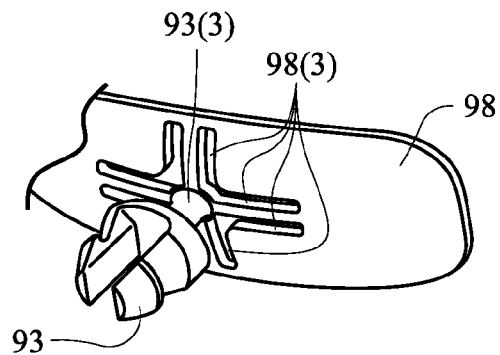

For example, FIGS. 25-1 to 25-5 show a pad support portion 98 attached to an attachment head 93 according to alternative examples of the disclosed technology. FIG. 25-1 shows an arrangement similar to that of FIG. 24 in which the attachment head 93 is coupled to the pad support portion 98 by a stem 93(3). In FIG. 25-2, the stem 93(3) includes a bowed or curved portion 93(3)-1 to enhance flexibility between the attachment head and the pad support portion. In FIG. 25-3, the pad support portion 98 includes elongated, parallel openings 98(3) to enhance flexibility at its connection with the stem 93(3). In FIG. 25-4, the stem 93(3) includes a longer and thinner configuration to enhance its flexibility. In FIG. 25-5, the pad support portion 98 includes a series of openings 98(3) in the shape of a cross to enhance flexibility at its connection with the stem 93(3). However, it should be appreciated that other suitable geometries are possible.

Figure 26:
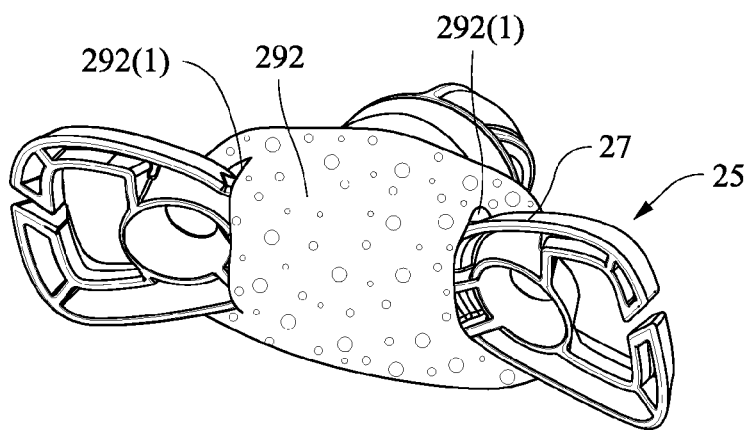
FIG. 26 is a perspective view of a forehead support and cushioning component according to an example of the disclosed technology.

FIG. 26 shows an alternative example in which a conformable cushioning component 292, e.g., constructed of foam, is wrapped over the existing forehead support plate 27 of the forehead support 25. As illustrated, the conformable cushioning component 292 may include slots 292(1) that allow respective ends of the forehead support plate to pass therethrough.

In the illustrated example of FIG. 23, the foam forehead support pad 92 is used along with a foam cushioning component 40, which provides a mask system having an all-foam patient contact. The foam forehead support pad may provide a softer feel on the patient's forehead, e.g., compared to silicone which can be relatively sticky. Also, the dial-type forehead support 25 as described above or any other forehead support adjustment mechanism may be used as the foam forehead support pad is conformable.

In the illustrated examples, the forehead support pad 92 is a separate component from the cushioning component 40. In an alternative example, one or more portions of the forehead support pad may be integrated with the cushioning component 40 and/or the cushion-to-frame component 50.

Forehead Support Pad Position on Forehead

In an example, the cushioning component may be structured to ensure that the forehead support pad is positioned substantially on the patient's forehead in use, i.e., cushioning component not sitting too low on the patient's face which may cause the forehead support pad to be positioned too low on the forehead or on the patient's eyebrows.

Figure 27:
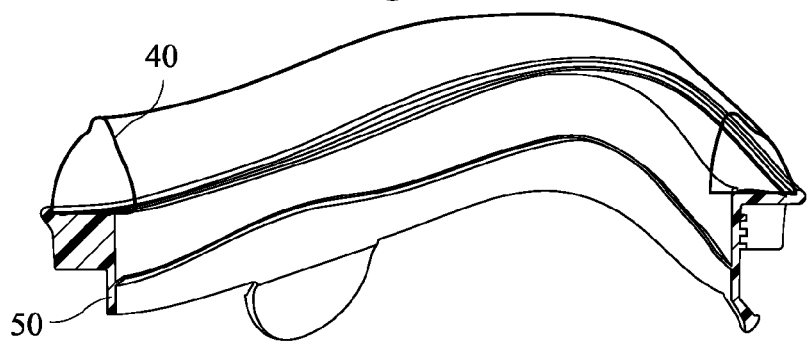
FIG. 27 is a cross-sectional view of a cushion-to-frame component and a foam-based interfacing structure according to an example of the disclosed technology.
Figure 28:
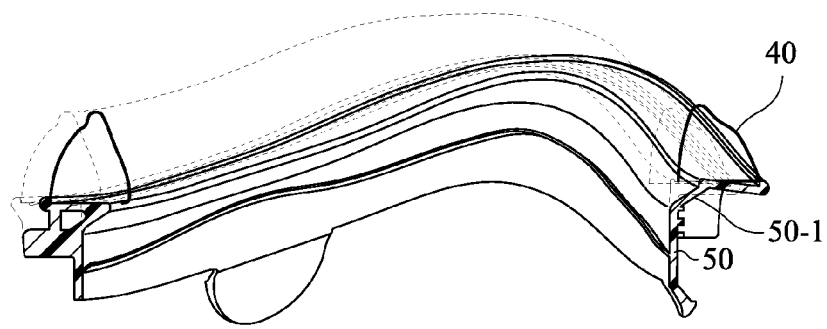
FIG. 28 is a cross-sectional view of a cushion-to-frame component and a foam-based interfacing structure according to another example of the disclosed technology.
Figure 29:
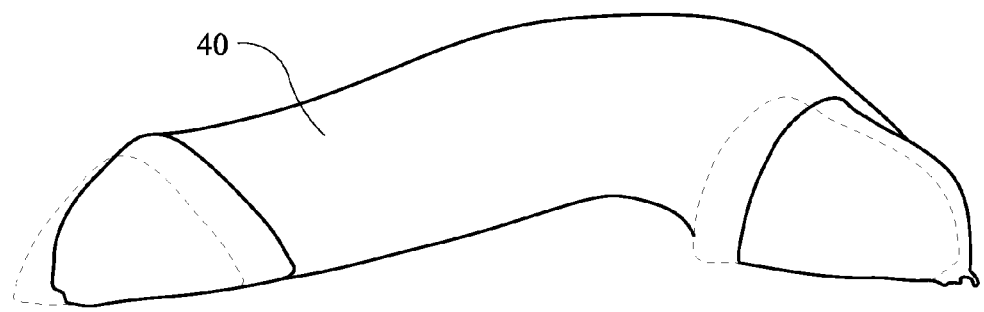
FIG. 29 is a cross-sectional view of a foam-based interfacing structure according to another example of the disclosed technology.
Figure 30:
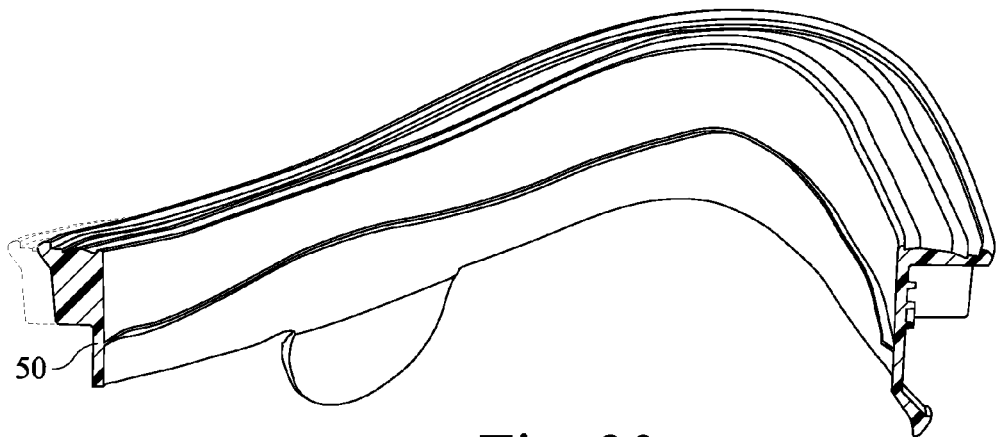
FIG. 30 is a cross-sectional view of a cushion-to-frame component according to another example of the disclosed technology.

For example, FIG. 27 is a cross-sectional view of a clip component 50 and cushioning component 40 according to an example of the disclosed technology. In FIG. 28, the cushion contacting side and platform thereof of the clip component 50 may be moved towards the patient's chin, e.g., by about 5 mm with respect to the clip component of FIG. 27. As illustrated, the inner wall of the clip component 50 includes an angled section 50-1 which allows the frame contacting side to maintain its position while allow the platform to be moved down towards the patient's chin. In FIG. 29, the position of the shims used to cut the foam cushioning component 40 may be changed to move the apex of the cushioning component at the nasal bridge and chin further up, i.e., towards the patient's forehead. In FIG. 30, the height of the clip component 50 may be reduced (measured from the nasal bridge region to the chin region).

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An interfacing structure for a mask system, comprising:
    a cushion component adapted to contact the patient's face in use; and
    a cushion-to-frame component provided to the cushion component, the cushion-to-frame component structured to secure the cushion component to a mask frame of the mask system,
    the cushion-to-frame component including a cushion side adapted to interface with the cushion component and a frame side adapted to interface with the mask frame,
    wherein the cushion side includes a platform including an inner flange and an outer flange provided to opposing ends of the platform and an engagement surface between the inner flange and the outer flange to engage the cushion component, and
    wherein the engagement surface is non-linear along its width and includes incline portions, decline portions, and flat portions along its width.
2. An interfacing structure according to claim 1, wherein the cushion component includes foam.
3. An interfacing structure according to claim 1, further comprising an adhesive to attach the cushion component to the cushion side.
4. An interfacing structure according to claim 1, wherein the frame side includes a pair of side clip portions and a bottom clip portion adapted to engage respective slots provided on the mask frame.
5. An interfacing structure according to claim 4, wherein the pair of side clip portions include a different structure or configuration than the bottom clip portion.
6. An interfacing structure according to claim 4, wherein each of the pair of side clip portions and the bottom clip portion extend from an inner wall of the cushion-to-frame component, the inner wall including one or more ribs adjacent each of the pair of side clip portions and the bottom clip portion structured and arranged to control flexibility of each of the pair of side clip portions and the bottom clip portion.
7. An interfacing structure according to claim 6, wherein at least one rib is provided adjacent the bottom clip portion.
8. An interfacing structure according to claim 6, further comprising side ribs and a central rib between the side ribs provided adjacent each side clip portion.
9. An interfacing structure according to claim 8, wherein the central rib is contoured along its length and protrudes further outwardly from the inner wall than the side ribs.
10. An interfacing structure according to claim 4, wherein the cushion-to-frame component includes a base portion adjacent each side clip portion, the base portion including one or more recesses or cut-outs.
11. An interfacing structure according to claim 1, wherein the cushion-to-frame component includes a sealing lip extending along an inner wall of the cushion-to-frame component, the sealing lip adapted to engage the mask frame and provide a seal.
12. An interfacing structure according to claim 11, wherein the sealing lip is provided between an upper surface and a lower surface of the inner wall, and the lower surface is offset outwards from the upper surface to increase a length of the sealing lip.
13. An interfacing structure according to claim 12, wherein a length of the sealing lip from the upper surface is about 2.2 mm and a length of the sealing lip from the lower surface is about 2.0 mm.
14. An interfacing structure according to claim 11, wherein the sealing lip includes a thickness of about 0.35 mm.
15. An interfacing structure according to claim 11, wherein the sealing lip includes an internal radius of about 0.1 mm.
16. An interfacing structure according to claim 11, wherein the sealing lip includes an angle of about 40-60° with respect to the inner wall.
17. An interfacing structure according to claim 1, wherein the cushion-to-frame component is molded of a thermoplastic elastomer (TPE).
18. An interfacing structure according to claim 1, further comprising arcuate-shaped protrusions or wings provided to respective sides of the cushion side of the cushion-to-frame component adjacent side of nose regions of the cushion component adapted to contact side of nose regions of the patient's face.
19. An interfacing structure according to claim 1, wherein the cushion component includes scalloped or inwardly curved surfaces in side of nose regions.
20. A mask system, comprising:
    a mask frame; and
    an interfacing structure according to claim 1 provided to the mask frame.

21. A mask system according to claim 20, further comprising a forehead support provided to the mask frame, the forehead support structured to carry at least one forehead support pad that is at least partially constructed of foam.

22. A mask system according to claim 21, wherein the forehead support pad includes a conformable cushioning component structured to contact the patient's forehead and an attachment component provided to the cushioning component and structured to secure the forehead support pad to the forehead support.

23. A mask system according to claim 22, wherein the attachment component is constructed of a material having greater hardness or structural integrity than the conformable cushioning component.

24. A mask system according to claim 22, wherein the cushioning component is attached to attachment component by an adhesive.

25. A mask system according to claim 22, wherein the cushioning component includes a pair of pads that are joined to one another by a bridge portion.

26. A mask system according to claim 22, wherein the attachment component includes a pair of pad support portions that are joined to one another by a bridge portion.

27. A mask system according to claim 22, wherein the attachment component includes an attachment head structured to attach the forehead support pad to the forehead support with a snap fit.

28. The mask system of claim 20, wherein the mask system is a full-face interface or a nasal interface.

29. An interfacing structure according to claim 1, wherein the engagement surface that is non-linear is further configured to shape the cushion component and retain the cushion component on the platform.

30. An interfacing structure according to claim 1, wherein non-linear engagement surface positively locates the cushion component, provides a larger surface area for retention, and defines one or more notches to define stop or retaining surfaces.

31. An interfacing structure according to claim 1, wherein the cushion component is attached to the platform by an adhesive, and the engagement surface that is non-linear is further configured to provide channels to receive the adhesive.

32. An interfacing structure according to claim 1, wherein the cushion component and the cushion-to-frame component are permanently connected.

33. An interfacing structure for a mask system for providing positive pressure respiratory therapy to a patient to treat a respiratory disorder, the interfacing structure comprising:
  a cushion component, the cushion component being constructed of foam and adapted to contact the patient's face in use, the cushion component having a nose bridge region configured to engage the patient's nose proximal to the patient's nose bridge in use, the cushion component having a pair of side of nose regions, and each of the side of nose regions configured to extend inferiorly from the nose bridge region and in opposite lateral directions relative to one another to engage a corresponding side of the patient's nose in use; and
  a cushion-to-frame component attached to the cushion component and structured to secure the cushion component to a mask frame of the mask system, the cushion-to-frame component comprising silicone, the cushion-to-frame component being relatively more rigid than the cushion component, the cushion-to-frame component further comprising a pair of lateral sides, and each of the lateral sides of the cushion-to-frame component further comprising a protrusion that is configured to extend posteriorly towards the patient such that a surface of the cushion component at each of the side of nose regions matches a shape of the protrusion of the cushion-to-frame component,
  wherein the cushion component further comprises a scalloped surface or an inwardly curved surface at each side of nose region and adjacent the protrusion to reduce an amount of foam near the patient's eyes, and
  wherein the cushion-to-frame component includes an attachment structure structured to mechanically interlock the cushion-to-frame component with the mask frame.

34. An interfacing structure according to claim 33, wherein the cushion-to-frame component includes at least one rib.

35. An interfacing structure according to claim 33, wherein the cushion-to-frame component is attached to the cushion component by an adhesive.

36. An interfacing structure according to claim 33, wherein the cushion component and the cushion-to-frame component are permanently connected.

37. An interfacing structure according to claim 33, wherein the cushion component and the cushion-to-frame component are curved at each side of nose region in a medial direction to avoid the patient's eyes.

38. An interfacing structure for a mask system for providing positive pressure respiratory therapy to a patient to treat a respiratory disorder, the interfacing structure comprising:
  a cushion component, the cushion component being constructed of foam, the cushion component including a face-contacting surface adapted to contact a region of the patient's face in use, the cushion component having a nose bridge region configured to engage the patient's nose proximal to the patient's nose bridge in use, the cushion component having a pair of side of nose regions, each of the side of nose regions configured to extend inferiorly from the nose bridge region and in opposite lateral directions relative to one another to engage a corresponding side of the patient's nose in use, and the cushion component including a cushion-to-frame component engagement surface; and
  a cushion-to-frame component attached to the cushion component and structured to secure the cushion component to a mask frame of the mask system, the cushion-to-frame component comprising silicone, the cushion-to-frame component including a cushion engagement surface structured to engage the cushion-to-frame component engagement surface of the cushion component, the cushion-to-frame component being more rigid than the cushion component, the cushion-to-frame component further comprising a pair of lateral sides and each of the lateral sides of the cushion-to-frame component further comprising a protrusion that is configured to extend posteriorly towards the patient such that the cushion-to-frame component engagement surface of the cushion component at each of the side of nose regions matches a shape of the protrusion of the cushion-to-frame component,
  wherein the cushion component further comprises a scalloped surface or an inwardly curved surface at each side of nose region and adjacent the protrusion to reduce an amount of foam near the patient's eyes.

39. An interfacing structure according to claim 38, wherein the cushion engagement surface is configured to impart different curvatures in different regions of the face-contacting surface of the cushion component along a perimeter of the face-contacting surface.

40. An interfacing structure according to claim 38, wherein the cushion engagement surface is structured to impart different shapes or angles in different regions of the cushion component.

41. An interfacing structure according to claim 38, wherein the cushion component and the cushion-to-frame component are permanently connected.

42. An interfacing structure according to claim 38, wherein the cushion component and the cushion-to-frame component are curved at each side of nose region in a medial direction to avoid the patient's eyes.

43. A method for manufacturing an interfacing structure for a mask system for providing positive pressure respiratory therapy to a patient to treat a respiratory disorder, the method comprising:
   providing a cushion component, the cushion component being constructed of foam, the cushion component having a cushion-to-frame component engagement surface, the cushion component having a face-contacting surface adapted to contact a region of the patient's face in use, the cushion component having a nose bridge region configured to engage the patient's nose proximal to the patient's nose bridge in use, the cushion component having a pair of side of nose regions, and each of the side of nose regions configured to extend inferiorly from the nose bridge region and in opposite lateral directions relative to one another to engage a corresponding side of the patient's nose in use; and
   providing a cushion-to-frame component to the cushion component, the cushion-to-frame component including a cushion engagement surface structured to engage the cushion-to-frame component engagement surface of the cushion component, the cushion-to-frame component structured to secure the cushion component to a mask frame of the mask system, the cushion-to-frame component comprising silicone, the cushion-to-frame component further comprising a pair of lateral sides, each of the lateral sides of the cushion-to-frame component further comprising a protrusion that is configured to extend posteriorly towards the patient such that the cushion-to-frame component engagement surface of the cushion component at each of the side of nose regions matches a shape of the protrusion of the cushion-to-frame component, and the cushion-to-frame component being more rigid than the cushion component,
   wherein the cushion component further comprises a scalloped surface or an inwardly curved surface at each side of nose region and adjacent the protrusion to reduce an amount of foam near the patient's eyes, and wherein the method further comprises assembling the cushion-to-frame component engagement surface of the cushion component to the cushion engagement surface of the cushion-to-frame component.

44. The method of claim 43, wherein the cushion component and the cushion-to-frame component are permanently connected.

45. The method of claim 43, wherein the cushion component and the cushion-to-frame component are curved at each side of nose region in a medial direction to avoid the patient's eyes.

46. A mask system for providing positive pressure respiratory therapy to a patient to treat a respiratory disorder, the mask system comprising:
   a mask frame;
   a cushion component formed from foam and adapted to contact the patient's face in use, the cushion component having a cushion-to-frame component engagement surface, the cushion component further comprising a face-contacting surface opposite the cushion-to-frame component engagement surface, the cushion component having a nose bridge region configured to engage the patient's nose proximal to the patient's nose bridge in use, and the cushion component having a pair of side of nose regions, each of the side of nose regions configured to extend inferiorly from the nose bridge region and in opposite lateral directions relative to one another to engage a corresponding side of the patient's nose; and
   a cushion-to-frame component formed from silicone, the cushion-to-frame component including a cushion engagement surface structured to engage the cushion-to-frame component engagement surface of the cushion component, the cushion-to-frame component being relatively more rigid than the cushion component, the cushion-to-frame component further comprising a pair of lateral sides, and each of the lateral sides of the cushion-to-frame component further comprising a protrusion that is configured to extend posteriorly towards the patient such that the cushion-to-frame component engagement surface of the cushion component at each of the side of nose regions matches a shape of the protrusion of the cushion-to-frame component, and
   wherein the cushion component further comprises a scalloped surface or an inwardly curved surface at each side of nose region and adjacent the protrusion to reduce an amount of foam near the patient's eyes.

47. The mask system of claim 46, wherein the cushion-to-frame component further comprises a platform, the cushion engagement surface formed on the platform to engage the cushion component.

48. The mask system of claim 46, wherein the cushion component and the cushion-to-frame component are joined together with an adhesive.

49. The mask system of claim 46, wherein the cushion-to-frame component further comprises at least one rib.

50. The mask system of claim 46, wherein the cushion-to-frame component includes an attachment structure configured to mechanically interlock the cushion-to-frame component with the mask frame.

51. The mask system of claim 46, wherein the mask system is a full-face interface or a nasal interface.

52. The mask system of claim 46, wherein the cushion component and the cushion-to-frame component are joined together permanently.

53. The mask system of claim 46, wherein the cushion component and the cushion-to-frame component are curved at each side of nose region in a medial direction to avoid the patient's eyes.

* * * * *